US005922327A

United States Patent [19]

Crabb et al.

[11] Patent Number: 5,922,327

[45] Date of Patent: Jul. 13, 1999

[54] EQUINE HERPES VIRUS GLYCOPROTEINS

[75] Inventors: Brendan Scott Crabb, Ascot Vale; Michael Justin Studdert, Balwyn, both of Australia

[73] Assignee: The University of Melbourne, Australia

[21] Appl. No.: 08/338,530

[22] PCT Filed: May 28, 1993

[86] PCT No.: PCT/AU93/00253

§ 371 Date: Jan. 25, 1995

§ 102(e) Date: Jan. 25, 1995

[87] PCT Pub. No.: WO93/24528

PCT Pub. Date: Dec. 9, 1993

[30] Foreign Application Priority Data

Jun. 1, 1992 [AU] Australia ........................................ 2716

[51] Int. Cl.[6] ........................ A61K 39/245; C07H 21/04; C07K 14/03; C12N 7/01

[52] U.S. Cl. ..................... 424/229.1; 435/975; 435/69.3; 436/94; 514/44; 530/350; 536/23.72

[58] Field of Search ........................ 424/229.1; 435/69.3, 435/975; 436/94; 514/44; 530/350; 536/23.72

[56] References Cited

FOREIGN PATENT DOCUMENTS

| | | |
|---|---|---|
| WO 90/01546 | 3/1989 | WIPO . |
| WO 92/01057 | 1/1992 | WIPO . |
| WO 92/02252 | 2/1992 | WIPO . |
| WO 94/03628 | 8/1993 | WIPO . |

OTHER PUBLICATIONS

Crabb, et al., "Identification of Equine herpesvirus 4 Glycoprotein G: A Type–Specific, Secreted Glycoprotein", *Virology*190(1): 143–54 (1992).

Colle III et al. "Open Reading Frames Encoding a Protein Kinase . . ." Virology 188, 545–557 (1992).

Telford et al. "The DNA Sequence of Equine Herpesvirus–1" Virology 189, 304–316 (1992).

*Primary Examiner*—Jeffrey Stucker
*Assistant Examiner*—Phuong T. Bui
*Attorney, Agent, or Firm*—Foley & Lardner

[57] ABSTRACT

Equine rhinopneumonitis and equine abortion are horse diseases caused by two distinct but antigenically related viruses designated as equine herpes virus 4 (EHV4) and equine herpes virus 1 (EHV1). Glycoprotein G (gG) epitopes of EHV1 and EHV4 of this invention allow for accurate, type-specific diagnosis of the infections despite extensive antigenic cross-reactivity between the two viruses.

37 Claims, 13 Drawing Sheets

FIG. 3A

ATTTGGGGTG GAGACGGCGT GGGCCGATAC TG TATAAAGT TGTACTACTT

ACCAGCCCAG TCAGTGTGCT GTAGTGCCAC CACCTGTAAA GCTGTGATAA

*PstI*
GCTGCAGGCA TATGTTGGCT GTGGGAGCAA CTCTGTGTTT ACTGAGTTTC
M L A V G A T L C L L S F 13

CTAACTGGCG CTACTGGACG GCTAGCTCCT GACGACCTCT GCTATGCAGA
L T G A T G R L A P D D L C Y A E 30

ACCCCGCAAA ACCGGTCCCA TGCCCCGCTC AAAACCTAAA CACCAACCCC
P R K T G P M P R S K P K H Q P L 47

TACTATTTGA AGCCCCAAAG GTTGCTCTTA CGGCAGAGTC AAAGGGTTGT
L F E A P K V A L T A E S K G C 63

CAACTAATAT TGTTAGACCC TCCAATAGAC ATGGGCTATC GCTTAGAGGA
Q L I L L D P P I D M G Y R L E D 80

CAAGATAAAC GCTTCCATTG CTTGGTTTTT TGACTTTGGT AATTGTCGAA
K I N A S I A W F F D F G N C R M 97

TGCCCATCGC ATACAGAGAG TACTATGATT GCGTTGGCAA CGCAATCCCA
P I A Y R E Y Y D C V G N A I P 113

TCTCCAGAAA CATGTGATGG TTACTCATTT ACACTTGTTA AAACAGAGGG
S P E T C D G Y S F T L V K T E G 130

TGTAGTTGAG TTTACCATCG TAAACATGAG CTTACTGTTG CAGCCTGGAA
V V E F T I V N M S L L L Q P G I 147

TATACGACAG TGGAAGTTTT ATATACAGCG CCCTTCTAGA TATGGATGTA
Y D S G S F I Y S A L L D M D V 163

TTGACTGGAC GCGTAATTTT GAACGTGGAG AACGACACTA ACTATCCATG
L T G R V I L N V E N D T N Y P C 180

CGGAATGACT CACGGCCTCA CTGCGGATGG CAACATCAAC GTAGATGAAA
G M T H G L T A D G N I N V D E T 197

CCACGCACAC AACCCCACAT CCACGTGCTG TCGGGTGTTT TCCAGAACTC
T H T T P H P R A V G C F P E L 213

FIG. 3B

ATTAACTTCG ATGCATGGGA AAACGTTACA TTCGAAGAAA TGGGGATACC
I N F D A W E N V T F E E M G I P 230

AGACCCAAAC TCATTTCTTG ATGATGAGAG TGATTACCCG AATACAATGG
D P N S F L D D E S D Y P N T M D 247

ACTGTTACTC GTGGGATTTA TACACATATC CCAAAAGCCT GAAGCAGGCA
C Y S W D L Y T Y P K S L K Q A 263

GAGGGGCCCC AAACCTTGTT AATAGGTGCA GTTGGACTCA GAATACTCGC
E G P Q T L L I G A V G L R I L A 280

GCAAGCATGG AAGTTTGTTG AAAATGAAAC CTACAGCAGC ATACGCGCAG
Q A W K F V E N E T Y S S I R A D 297

ATGCTAAGGA GTTGATGTTA CACAGCCAGT CCTGTACAGC TGATTCGTCG
A K E L M L H S Q S C T A D S S 313

CAAGAAAGCA CATCTATGAA GAATAACCCT ATTTATTCAG AGGGGAGCCT
Q E S T S M K N N P I Y S E G S L 330

CATGCTAAAC GTTCAGCACG ATGACAGCAT CCACACGGAA GGGATGAAGA
M L N V Q H D D S I H T E G M K N 347

ATAACCCTGT TTATTCAGAG AGCCTCATGC TAAACGTCCA GCACGATGAC
N P V Y S E S L M L N V Q H D D 363

AGCATCCACA CCGGGGGTGT GTTGCATGGC CTCCAAGACT GCGACAACCA
S I H T G G V L H G L Q D C D N Q 380

GCTCAAAACT GTGTATATTT GCCTAGCTCT TATTGGACTC GGCACATGTG
L K T V Y I C L A L I G L G T C A 397

CCATGATAGG ACTAATAGTT TACATTTTTG TGCTAAGGTC AAAAATATCT
M I G L I V Y I F V L R S K I S 413

TCCCACAATT TATCGCGCTC ACAAAATGTA AAACATAGAA ACTATCATCG
S H N L S R S Q N V K H R N Y H R 430

ACTTGAGTAC GTTGCATAAT ACATGTCAAA TAAAAGTTAA AAATTAAACA
L E Y V A 435

TTGTTGTCTG TAATAACTGA GTGTGGTTTT AAAAAATACT AAATCGCGGC

FIG. 5a(1)

```
EHV4.405/76 gG   MLAVGATLCLLSFLTGATGRLAPDDLCYAEPRKTGPMPRSKPKHQPLLFEAPKVALTAES    60
EHV1.438/77 gG   MLTVLAALSLLSLLTSATGRLAPDELCYAEPRRTGSPPNTQPERPPVIFEPPTIAIKAES    60

EHV4.405/76 gG   KGCQLILLDPPIDMGYRLEDKINASIAWFFDFGNCRMPIAYREYYDCVGNAIPSPETCDG   120
EHV1.438/77 gG   KGCELILLDPPIDVSYRREDKVNASIAWFFDFGACRMPIAYREYYGCIGNAVPSPETCDA   120

EHV4.405/76 gG   YSFTLVKTEGVVEFTIVNMSLLLQPGIYDSGSFIYSALLDMDVLTGRVILNVENDTNYPC   180
EHV1.438/77 gG   YSFTLIRTEGIVEFTIVNMSLLFQPGIYDSGNFIYSVLLDYHIFTGRVTLEVEKDTNYPC   180

EHV4.405/76 gG   GMTHGLTADGNINVDETT-HTTPHPRAVGCFPELINFDAWENVTFEEMGIPDPNSFLDDE   239
EHV1.438/77 gG   GMIHGLTAYGNINVDETMDNASPHPRAVGCFPEPIDNEAWANVTFTELGIPDPNSFLDDE   240
```

FIG. 5a(2)

```
EHV4.405/76 gG   SDYPNTMDCYSWDLYTYPKSLKQAEGPQTLLIGAVGLRILAQAWKFVENETYSSIRADAK   299
EHV1.438/77 gG   GDYPNISDCHSWESYTYPNTLRQATGPQTLLVGAVGLRILAQAWKFVGDETYDTIRAEAK   300

EHV4.405/76 gG   ELMLHSQSCTADSSQESTSMKNNPIYSEGSLMLNVQHDDSIHTEGMKNNPVYSESLMLNV   359
EHV1.438/77 gG   NLETHVPSSAAESSLENQS----------------------TQEESNSPEVAH--LRSV   336

EHV4.405/76 gG   QHDDSIHTGGVLHGLQDCDNQLKTVYICLALIGLGTCAMIGLIVYIFVLRSKISSHNLSR   419
EHV1.438/77 gG   NSDDSTHTGGASNGIQDCDSQLKTVYACLALIGLGTCAMIGLIVYICVLRSKLSSRNFSR   395

EHV4.405/76 gG   SQNVKHRNYHRLEYVA   435
EHV1.438/77 gG   AQNVKHRNYQRLEYVA   411
```

EQUINE HERPES VIRUS GLYCOPROTEINS

INTRODUCTION TO INVENTION

This invention relates to Equine Herpesvirus and in particular to type-specific glycoproteins thereof and diagnostic tests and clinical applications associated with the characterization of such glycoproteins.

BACKGROUND OF INVENTION

Equine rhinopheumonitis and equine abortion are commonly recognised diseases of horses caused by two distinct but antigenically related viruses that are designated equine herpesvirus 4 and equine herpesvirus 1, known as EHV4 and EHV1 respectively. Because the viruses are related antigenically it has not been possible to date by serological examination (blood test), to determine whether a horse has been infected with either or both EHV4 or EHV1. For example, if a horse had been infected with EHV4 as a foal it would develop antibodies in its serum that would react with not only EHV4 but with EHV1 as well, so one would not know that such a foal had been infected with only EHV4.

However, since 1981 it has been repeatedly shown that the restriction endonuclease fingerprints of the two viruses are distinctly different with respiratory isolates and fetal isolates almost invariably typing as EHV4 and EHV1 respectively. The availability of specific monoclonal antibodies (MAbs) directed to either EHV4 or EHV1 has also allowed consistent and specific typing of isolates of the two viruses.

The major significance in developing a specific antibody test relates to the fact that both these herpesviruses are believed, after primary infection, to establish a persistent, latent and life-long infection. Either virus may from time to time be reactivated from the latent state (just as is the case with recurrent cold sores in humans infected with herpes simplex virus); the virus, reactivated from the latent state, will usually cause recurrent disease in the host horse but more importantly such a horse will either directly or indirectly by contact act as a source of infection for other horses. In this way, for EHV4, there is usually in the annual foal crop born on a farm an annual round of respiratory disease ("snotty" noses). Such an occurrence is almost an accepted part of breeding horses. Occasionally foals become severely affected and require treatment or die because of severe secondary complications such as bacterial pneumonia.

While the natural history of EHV1 is less clearly understood, there is an assumption that the virus does establish persistent, lifelong latent, infections. Upon reactivation there may be a further bout of respiratory disease. However, a far more serious consequence for other horses infected by contact with the first horse (index case) occurs on breeding farms when a pregnant mare in a paddock reactivates the virus and transmits it to other in-contact pregnant mares. The index case mare may herself abort or cause abortion in one or more in contact mares. An aborted foetus and the foetal membranes and fluids are heavily infected with EHV1 and contaminate the site where abortion occurs.

Other mares in the paddock, being naturally curious, come to the site of abortion and sniff the foetus and membranes. In this way, often close to 100% of the mares in the paddock become infected and abort within 10 or 20 days causing what is commonly known as an "abortion storm". Such outbreaks of EHV1 abortion are of considerable economic importance to the equine, particularly thoroughbred and standardbred, industries worldwide.

There is a need for accurate, type-specific serological surveillance of horses for the presence of EHV4 and/or EHV1 antibodies to assist in our understanding of the epidemiology of these viruses, particularly EHV1. Presently, however, EHV1 or EHV4 antibodies in polyclonal serum cannot be differentiated because of the extensive antigenic cross-reactivity between the two viruses. The availability of such a specific serological test would also have profound implications in the control, perhaps eradication, of EHV1 and in the selection of candidate horses for vaccination.

The antibody responses of the horse to these viruses is largely directed to the envelope glycoproteins. EHV1 homologues to nine of the ten recognized herpes simplex virus 1 (HSV1) glycoproteins have been identified from DNA sequence analyses; gB, gC, gD, gE, gG, gH, gI, gK, and gL. The remaining HSV1 glycoprotein, gJ, has a positional counterpart in the US region of EHV1, gene 71, although these two genes do not show any significant homology. Also, EHV1 possesses at least three other glycoproteins designated gp2, gp10, which are the homologues of the HSV1 tegument proteins VP13/14 and gp21/22a. In the case of EHV4, which unlike EHV1 has only been partially sequenced, glycoprotein genes encoding gB, gC, gG and gH homologues have been identified which show amino acid identities of 89%, 79%, 58% and 85% respectively with their EHV1 counterparts. Homologous EHV4 and EHV1 genes map to collinear positions in their respective genomes.

EHV1 glycoproteins gp2, gp10, gC (gp13), gB (gp14), gD (gp18) and gp21/22a have been definitively identified by SDS-PAGE as have EHV4 glycoproteins gp2, gp10, gC (gp13), gB (gp14), gD (gp18) and gG. Using combinations of EHV1/EHV4 MAbs and polyclonal post-EHV1 only or post-EHV4 only horse sera it has been shown that each of the glycoproteins possesses both type-common and type-specific epitopes The two exceptions are gp21/22a which has been relatively poorly studied and EHV4 gG which appears to elicit a type-specific serological response.

To date, glycoprotein G (gG) homologues of other herpesviruses have been used as a basis for diagnostic testing and clinical application. In particular, gG (alternatively called gX) of pseudorabies virus (PRV) has been used in the development of gG deletion mutant vaccines linked to a diagnostic test for PRV of pigs.

Also gG of human herpes simplex viruses (HSV) 1 and 2 are different enough to allow tests such as ELISA to be developed for the detection of antibodies to either HSV1 or 2 in the serum of humans.

However, in spite of these data for PRV and HSV 1 and 2 it could not have been predicted that the same glycoprotein, namely glycoprotein G of EHV4 and EHV1, would serve a role in diagnosis and vaccine development. For PRV, only a single virus is involved, so the question of distinguishing between two viruses is not relevant. For HSV 1 and 2, while two viruses are involved, the gG proteins are different in very different ways from EHV4 and EHV1 gGs. In particular, the molecular sizes of unglycosylated HSV1 and HSV2 gGs differ greatly with HSV1 at 26K and, HSV2 at 77K, whereas the sizes of unglycosylated EHV4 and EHV1 gG differ only slightly at 48K and 45K respectively. It is reasoned that the type-specificity of the entire HSV1 and 2 gG proteins resulted from a major deletion in the case of the HSV1 gG gene whereby some 1383 nucleotides have been "lost" from a total gene (in the case of HSV2) of 2097 nucleotides. The loss of more than half the coding sequence of HSV1 gG results in a non glycosylated protein of only 26K vs 77K for HSV2 gG. While it is recognised that a positive ELISA is required for the differentiation of humans infected with either HSV1 or 2 it could have been reasoned that if the two genes were of approximately the same size then the two gGs would be cross-reactive. For EHV4 and EHV1 it is shown that while the two gGs are approximately the same size they are still type-specific. This could not have been predicted from prior art (HSV) material or from sequence data alone. On the later point the fact that EHV4 and EHV1 gG are 58% similar at the amino acid level it could in fact have been predicted that cross-reactive epitopes would almost certainly have existed and hence gG could not have been used in the concurrently described invention to differentiate the two equine viruses. The findings of the current invention are based on the analysis of a specifically selected set of horse serums for which the previous infection/vaccination history of particular horses was known. Detailed analysis of these scrums show that cross-reactive epitopes are either not present or are not important in eliciting an antbody response in the natural host. Such a highly distinctive property of these epitopes was quite unexpected and has allowed the development of the instant invention.

OBJECT AND STATEMENT OF INVENTION

One object of this invention is to characterize a protein or protein set or derivatives thereof that are capable of applications in the diagnosis and differentiation of EHV4 and EHV1.

A second object of this invention is to provide immunological agents associated with the control of EHV4 and EHV1.

A third object of this invention is to provide diagnostic methods, tests, reagents and peripherals associated with the diagnosis and differentiation of EHV4 and EHV1.

Accordingly the invention provides, in one broad aspect, envelope glycoproteins of equine herpesvirus capable of distinguishing equine herpesvirus 4 and equine herpesvirus 1.

The glycoproteins arc preferably type-specific to EHV4 and EHV1 invoking minimal or negligible cross-reaction and incorporating minimal or negligible type-common epitopes between EHV4 and EHV1.

The glycoproteins most preferably belong to the glycoprotein set G, known as gG, being EHV4 gG pertaining to EHV4 and EHV1 gG pertaining to EHV1.

EHV4 gG is secreted into the medium of infected cell cultures. EHV1 gG has not been observed as a secretion into the medium of infected cells.

The EHV4 gG glycoprotein preferably comprises a 435 amino acid sequence corresponding to an unglycosylated Mr value of 48 kilodaltons.

The EHV1 gG glycoprotein preferably comprises a 411 amino acid sequence corresponding to an unglycosylated Mr value of 45 kilodaltons.

The EHV4 gG is preferably characterized by the following amino acid sequence: (SEQ ID NO:2)

or subsequences thereof capable of eliciting a type-specific response including naturally occurring derivatives, variants, genetically engineered derivatives, glycosylated forms of the proteins or synthetically made derivatives.

The EHV4 gG gene is characterized by a coding region comprising the following nucleotide sequence: (SEQ ID NO:1)

or degeneracy equivalents or subsequences thereof coding for amino acid sequences or epitopes capable of eliciting a type-specific response.

The EHV1 gG is preferably characterized by the following amino acid sequence: (SEQ ID NO:3)

or subsequences thereof capable of eliciting a type-specific response including naturally occurring derivatives, variants, genetically engineered derivatives, glycosylated forms of the proteins or synthetically made derivatives. Preferably the epitopes responsible for eliciting the type-specific response are encompassed by EHV4 gG amino acids 287–374 and EHV1 gG amino acids 288–350 (as herein defined).

Most preferably the EHV4 epitope is characterized by the amino acid sequence:(SEQ ID NO:4)

or subsequences thereof capable of eliciting a type-specific response including naturally occurring derivatives, variants, genetically engineered derivatives, glycosylated forms of the proteins or synthetically made derivatives.

An alternative EHV4 epitope is characterized by the following amino acid sequence (SEQ ID NO:5)

KTGPMPRSKPKHQPLLFEAPKVALT or subsequences thereof capable of eliciting a type-specific response including naturally occurring derivatives, variants, genetically engineered derivatives, glycosylated forms of the proteins or synthetically made derivatives.

The invention further provides EHV4 discontinuous epitopes characterized by a discontinuous combination of the above detailed epitopes or derivatives of these 2 regions, either alone or together, with other regions of the EHV4 gG molecule.

The invention further provides plasmid vector pEG4var (as herein defined).

Most preferably the EHV1 epitope is characterized by the following amino acid sequence (SEQ ID NO:6)

GDETYDTIRAEAKNLETH-VPSSAAESSLENQSTQEESNSPEVAHL-RSVNSDDSTHTGG ASNGI or subsequences thereof capable of eliciting a type-specific response including naturally occurring derivatives, variants, genetically engineered derivatives, glycosylated forms of the proteins or synthetically made derivatives.

An alternative EHV1 epitope is characterized by the following amino acid sequence. (SEQ ID NO:7)

RTGSPPNTQPERPPVIFEPPTLATK or subsequences thereof capable of eliciting a type-specific response including naturally occurring derivatives, variants, genetically engineered derivatives, glycosylated forms of the proteins or synthetically made derivatives.

The invention further provides EHV1 discontinuous epitopes characterized by a discontinuous combination of the above detailed epitopes or derivatives of these 2 regions, either alone or together, with other regions of the EHV1 gG molecule.

The invention further provides a plasmid vector pEG1var (as herein defined).

The invention further provides vaccines for the immunization of horses against EHV4 and/or EHV1.

Among the various vaccine types possible are deletion mutant vaccines characterized by the deletion of EHV4 gG amino acids 287–374 and/or deletion of EHV1 gG amino acids 288–350 or subsequences thereof or amino acids located elsewhere in the gG that are either directly or indirectly capable of eliciting a type-specific response.

The vaccine may alternatively be an insertion mutant vaccine utilizing the promotor of gG. In a preferred form DNA coding for equine influenza virus haemagglutinin antigen or other equine virus antigens including equine influenza neurimidase or nucleoprotein antigens or derivatives thereof are inserted into EHV4 or EHV1 “downstream” of the gG promotor. In another preferred form DNA coding for any one, or a combination of, equine arteritis virus, equine rhinovirus and equine adenovirus is inserted into the EHV4 or EHV1 "downstream" of the gG promotor. Alternatively, the gG deleted gene location could be used for insertion and expression of foreign genes driven by other foreign promoters.

Numerous alternative vaccine products are included in the scope of the invention.

The invention further provides an immunological test kit characterized by antigens in the form of envelope glycoproteins capable of distinguishing horses infected with equine herpesvirus 4 and equine herpesvirus 1. The antigens can be any of the envelope glycoproteins or epitopes as hereinbefore described but are most preferably EHV4 gG amino acids 287–374 and EHV1 gG amino acids 288–350. Any subsequences of the above epitopes capable of eliciting typespecific responses are also particularly preferred as capture antigens.

The invention further provides numerous immunological tests and methods utilizing the unexpected highly distinctive properties of the above described EHV4 and EHV1 epitopes.

In particular the invention provides an immunological test method comprising at least the following steps:

a) Antibody contained in horse serum is added to a filter paper disc and allowed to react with EHV4 gG or EHV1 gG capture antigens;

b) Following washing a second anti-species antibody conjugated to an enzyme marker is added to the filter paper and allowed to react with any specifically bound horse antibody;

c) After a further washing, an enzyme substrate capable of generating a signal is added.

The invention further provides a method of testing for EHV4 and EHV1 infected horses comprising the detection of wild type EHV4 and/or EHV1 characterized by the presence of EHV4 gG and/or EHV1 gG.

The method also allows the testing for a horse vaccinated against EHV4 and/or EHV1 by the detection of EHV4 and/or EHV1 characterized by the absence of EHV4 gG and or EHV1 gG.

The method also allows the testing for a horse not infected with or vaccinated against EHV4 or EHV1 by the detection of the absence of EHV4 gG and EHV1 gG antibodies. The testing methods may use EHV4 gG and EHV1 gG antigens in combination with other equine herpesvirus glycoproteins.

In another aspect, the invention provides antibodies to the above described envelope glycoproteins capable of distinguishing equine herpesvirus 4 and equine herpesvirus 1. The antibodies are most preferably monoclonal and raised against the EHV4 gG epitope comprising the amino acid sequence 287–374, or subsequences thereof capable of eliciting a type-specific response. Similar monoclonal antibodies may be raised against the EHV1 gG epitope comprising the amino acid sequence 285–350, or subsequences thereof capable of eliciting a type-specific response.

In yet another aspect, the invention provides nucleic acid hybridization probes to the EHV4 and EHV1 gG epitope nucleotide sequences.

DETAILED DESCRIPTION OF THE INVENTION

The invention will now be more fully described with reference to FIGS. 1 to 13 as follows:

BRIEF DESCRIPTION OF THE DRAWINGS

FIG. 1 Identification and characterisation of proteins found in the supernatant (S/N) of EHV4 and EHV1 infected cell cultures.

FIG. 2 Strategy for determining the nucleotide sequence of the US region EHV4 DNA located near the internal repeat structure.

FIGS. 3A and 3B Nucleotide sequence and predicted amino acid sequence of ORF4 and flanking regions (SEQ ID NOS:1–2, respectively). Amino acids are given in single letter code and are numbered, from the first methionine residue, on the right. The TATA box, Pst 1 site, polyadenylation signal and GT-rich region following the polyadenylation signal are underlined sequentially. Potential asparagine (N)-linked glycosylation sites (N-X-S/T) are indicated by asterisks (*) and the proposed proteolytic cleavage site at amino acid residue 19 is indicated by a slash (/).

FIG. 4 Expression of EHV4 gG in *E. coli*.

FIGS. 5(*a*)(1) and (*a*)(2) Alignment of the amino acid sequences (SEQ ID NOS:2–3, respectively) of EHV4.405/76 gG with EHV1.Ab4p gG as determined by Telford et al (1992). The amino acid numbers are indicated on the right. Predicted signal sequence and transmembrane sequence at the N- and C-termini respectively are indicated by the dashed lines. Potential N-linked glycosylation sites (N-X-S/T) are indicated by the balloons with the filled balloon indicating a site conserved in the gG homologues of PRV, HSV2 and ILTV. The cysteine residues conserved between EHV4 gG and EHV1 gG and also in the gG homologues of PRV, HSV2 and ILTV are boxed. A near perfect repeated sequence in EHV4 gG is indicated by the arrows.

SUMMARY OF DETAILED DESCRIPTION

Figures 1A, 1B, 1C, 1D:
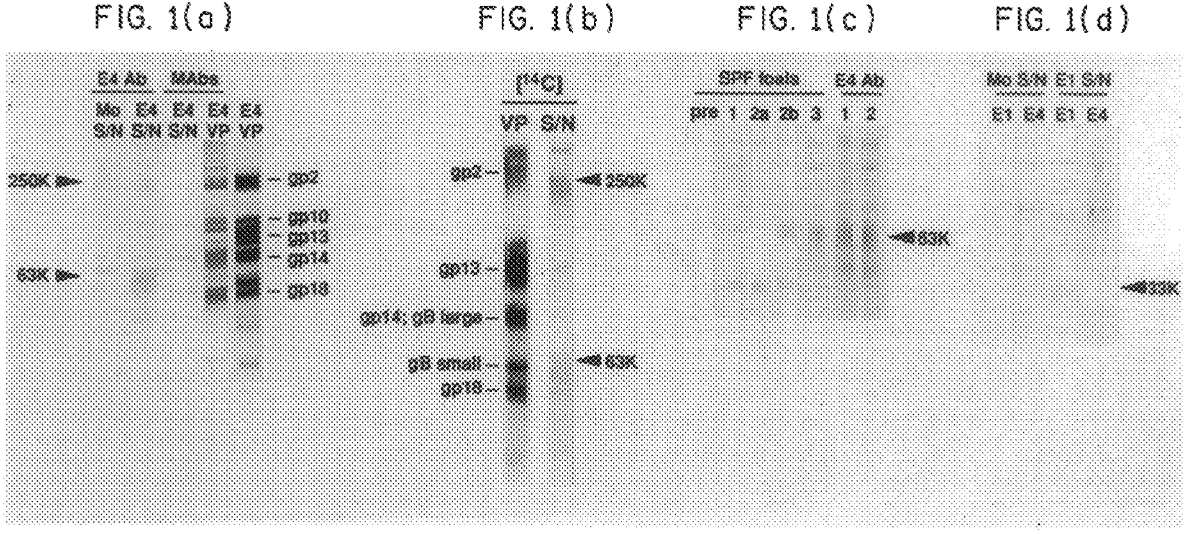
FIG. 1A EHV4 S/N proteins (E4 S/N) or EHV4 purified virion proteins (E4 VP) were separated on a 10% polyacrylamide gel and transferred to PVDF membranes. Mock infected cell culture supernatant (Mo S/N) was included as a control. The S/N proteins were probed with either a pool of monospecific, polyclonal post-EHV4 horse sera or a pool of 4 monoclonal antibodies (MAbs) directed to EHV4 gp2, gp10, gp14 or gp18. The lane to the far right represents an flourograph of a PVDF membrane containing [$^{14}$C]glucosamine labelled EHV4 virion proteins. The EHV4 secreted proteins detected by the polyclonal sera are indicated by arrows and the major EHV4 glycoproteins are indicated at the right.
FIG. 1B Flourographs of [$^{14}$C] glucosamine labelled E4 VP or S/N proteins after separation on a large polyacrylamide gel (16×16×0.75 cm). Labelling of the major glycoproteins and the secreted products is as above.
FIG. 1C Westem blot of EHV4 S/N proteins probed with sera derived from SPF foals that were either immunized with EHV1 (SPF foal 1), experimentally infected with EHV1 (SPF foal 2a) and later cross-challenged with EHV4 (SPF foal 2b) or immunized with EHV4 (SPF foal 3) and with sera from two previously seronegative horses that were experimentally infected with EHV4 (post-EHV4 infection horses 1 and 2; E4 Ab1 and E4 Ab2). A pool of sera taken from the three SPF foals prior to immunization or infection is included (pre).
FIG. 1D Western blot of S/N from cell line grown EHV1 (E1 S/N) or mock infected cell cultures (Mo S/N) both probed with either a pool of post-EHV1 sera which includes sera from foal 1 and foal 2a (E1) or a pool of post-EHV4 sera which includes sera from foal 3 and post-EHV4 infection horse 2 (E4).

Equine herpesvirus 4 (EHV4) glycoproteins of Mr 63K and 250K were identified in the supernatant of infected cell cultures. The 63K glycoprotein was type-specific, that is, it reacted with monospecific sera from horses that had been immunized or infected with EHV4, but not with monospecific sera from horses immunized or infected with EHV1, a closely related alphaherpesvirus. It was proposed that the secreted protein may, in fact, be the homologue of similarly secreted glycoproteins of herpes simplex virus 2 glycoprotein G (HSV2 gG) and pseudorabies virus (PRV) gx, which is the homologue of HSV2 gG notwithstanding the highly similar nature of EHV4 and EHV1 glycoprotein when compared to the HSV and PRV glycoproteins which would teach away from the expectation of such a result. The US region of the EHV4 genome, toward the internal repeat structure, was sequenced. Four open reading frames (ORFs) were identified of which ORF4 showed 52% similarity to the gene encoding PRV gX in a 650 nucleotide region. ORF4 coded for a primary translation product of 435 amino acids which has a predicted size of 48 kilodaltons (K). The amino acid sequence of ORF4 showed 28% identity with PRV gX and 16% identity with HSV2 gG, although significantly greater identity was observed in the N-terminal region including the conservation of 4 cysteine residues. Accordingly, we designate ORF4 as EHV4 gG. The predicted amino acid sequence of the EHV4 gG showed characteristics of an envelope glycoprotein. Expression of the entire EHV4 gG gene in the bacterial expression vector pGEX-3X produced a type-specific fusion protein of Mr 70K of which the gG portion comprises 43K. Antibody that was affinity purified from selected portions of Western blots containing the 70K gG fusion protein reacted with the 63K secreted glycoprotein. Conversely, antibody affinity purified to the 63K secreted product reacted with the 70K gG fusion protein. These results showed that the EHV4 63K secreted glycoprotein was EHV4 gG, the third alphaherpesvirus gG homologue known to be, at least in part, secreted. The antigenicity of full and partial length EHV4 gG and EHV1 gG molecules expressed in *E. coli*.was determined. Fusion proteins comprising full length EHV4 gG (435 amino acids) or EHV1 gG (411 amino acids) reacted strongly and type-specifically with pooled post-EHV4 only or -EHV1 only horse sera respectively. A fusion protein containing amino acids 1–310 of EHV1 gG was not immunoreactive with the post-EHV1 horse sera thereby localising the immunoreactive epitope(s) to the C-terminal portion of the molecule. It was postulated that the type-specific epitopes were located within the highly variable regions comprising amino acids 287–374 of EHV4 gG and 288–350 of EHV1 gG. Fusion proteins expressing these variable regions reacted strongly and type-specifically with a panel of post-EHV4 and/or post-EHV1 horse sera. These fusion proteins, which were easily purified and produced in large amounts, provided the basis for the development of diagnostic serological assays such as ELISA to distinguish EHV4-, EHV1- and dual-infected horses.

MATERIALS AND METHODS

Cells and viruses

Virus strains EHV4.405/76 and EHV1.438/77 at passages 5 and 3 were grown in equine fetal kidney (EFK) cells respectively as described elsewhere. Purification of virions was also carried out as described previously. Infected ccll culture supernatant was prepared by infecting cells as described previously except that after virus adsorption the cells were washed twice with Hank's balanced salt solution before the addition of serum free maintenance medium. The supernatant was collected at 16 h post infection, clarified at 2,500×g for 10 mins then centrifuged at 100,000×g for 60 mins and stored at −20° C. until required.

Antibodies

MAbs IG12, 13A9, 3F6 and 20C4, directed against EHV4 gp2, gp10, gp14 (gB, large subunit) and gp18 (gD) respectively, were provided by G. P. Allen (university of Kentucky, Lexington, Ky., USA). Monospecific antisera to EHV4 and EHV1 were obtained from colostrum-deprived, SPF foals after a series of immunizations and challenges with either EHV1 (foal 1) or EHV4 (foal 3). Post-EHV4 only and post-EHV1 only horse sera were obtained from colostrum-deprived, specific-pathogen-free (SPF) foals after a series of immunizations and challenges with either EHV1 (foal 1 serum) or EHV4 (foal 3 serum). Another post-EHV1 only horse serum was obtained from a third SPF foal that was experimentally infected with EHV1 (foal 2a serum). This foal was later cross-challenged with EHV4 (foal 2b serum). Post-ERV4 only sera were also obtained from three previously seronegative horses that were experimentally infected with EHV4, termed post-EHV4 Nos. 1, 2 and 3. Sera were also obtained from two mares that had aborted as a result of EHV1 infection either 5 weeks (post abortion mare 1) or 1 year (post abortion mare 2; see Table 2). A serum was also obtained from a foal which had been experimentally infected intrauterinally with EHV2 and which possessed high antibody titers to this virus.

Western blots

Sodium doedecyl sulphate-polyacrylamide gel electrophoresis (SDS-PAGE) and electrophoretic transfer of viral proteins to Immobilon polyvinylidene fluoride (PVDF; Milipore) membranes were carried out as described previously. The PVDF membranes were cut into strips and probed in either 2 ml wells or small trays, depending on the size of the membrane strip, with either, MAbs diluted 1/1000 in antibody diluent (phosphate-buffered saline (pH 7.5) containing 0.05% (v/v) Tween-20 (PBST) with 5 mg/ml bovine serum albumin ($BSA_5$) and 5% goat serum), polyclonal sera diluted 1/1000 or affinity purified antibody (as described below) for 1 h at room temperature. Membranes were then washed for 15 mins with PBST. The primary antibody was detected with either a 1/1000 dilution of affinity purified rabbit anti-mouse IgG (Dako Immunoglobulins) or a 1/300 dilution of an affinity purified goat anti-horse IgG (Kirkegaard and Perry Laboratories Inc.), both conjugated with horseradish peroxidase, where appropriate. The blots were washed again with PBST and developed using a 3'3'diaminobenzidine (DAB) substrate (Sigma).

ELISA

ELISA's were carried out in 96 well polyvinyl chloride microtitre plates (Nunc-Immunoplate Maxisorp). The plates were washed 4 times between each step with PBST and incubated with volumes of 100 μl/well on a shaker for 1 h unless otherwise stated. Wells were coated with approximately 10 μg/ml purified virus, 0.5 μg/ml glutathione-S transferase (GST; see below) fusion protein or cell culture supernatant diluted 1/5 in 0.05M carbonate-bicarbonate buffer (pH 9.6) overnight at 4° C. Unoccupied sites were blocked by incubation for 2 h with $BSA_5PBS$ containing 5% goat serum (200 μl/well). Serial dilutions of polyclonal horse sera were then made in the wells using $BSA_5PBST$ containing 5% goat serum as diluent. Horseradish peroxidase-conjugated affinity purified goat anti-horse IgG (Kirkegaard and Perry Laboratories Inc.), diluted 1/1000 in antibody diluent, was added to each well. Plates were developed using a soluble TMB substrate (Sigma) and read spectrophotometrically, after 15 mins incubation at room temperature without shaking, at 450 nm using a Titertek Multiskan MC3 (Flow Laboratories).

DNA cloning and sequencing

Cloning of the subfragments of the EHV4 Eco RI G fragment has been described previously. *E. coli* strain DH5α was used to maintain the clones HS (2 kb) and G19 (3.4 kb). In order to determine the complete sequence of the clones a nested set of deletions was generated for each strand using the Erase-a-base system (Promega). After religation, the deleted plasmid DNA was used to transform competent *E. coli* (DH5α). The relevant deletion clones were selected and sequenced using the dideoxy chain termination method using modified T7 DNA polymerase (Pharmacia, Uppsala, Sweden) and [$^{35}$S]-dATP (Amersham). Sequencing reactions were electrophoresed in 6% polyacrylamide wedge gels. In addition, internal oligonucleotide sequencing primers were synthesized and used to fill in gaps in the sequence.

DNA sequence analysis

DNA sequence data analysis was performed using the Geneworks software package (IntelliGenetics, Mountain View, Calif., USA). Sequence similarity searches were made in the GenBank database using the FAST A programs of Pearson and Lipman (1988).

Preparation of EHV4 gG and EHV1 gG recombinant plasmids.

The bacterial expression plasmids pGEX-3X or pGEX-2T (AMRAD, Hawthorn Australia) were used to express the EHV4 gG and EHV1 gG genes from strains 405/76 and 438/77 respectively. Restriction endonuclease digestion and ligation of DNA as well as $CaCl_2$ transformation of competent *E. coli* were carried out according to Sambrook et al. For the derivation of clones pEG4var and pEG1var (see below) transformation was performed using the Gene-Pulser Electroporator (Bio-Rad). The EHV1.438/77 Bam HI D fragment, which encompasses much of the EHV1 US region (FIG. 6), was cloned into pUC-19 following purification of the fragment from an agarose gel slice using Prep A Gene matrix and buffers (Bio-Rad). The nucleotide sequence of the first and last 200–300 bases of each recombinant expression plasmid was determined to ensure correct identity, orientation and frame of the cloned gene (data not shown). The following recombinant plasmids (see also FIG. 6) were constructed:

(i) pEG4.1 which was derived from a pUC-18 deletion clone, designated 18S/E, which was derived in the course of DNA sequencing by utilizing a Pst I site located just upstream from the start of the gG gene. The plasmid contained a 1.5 kilobase pair insert within which was the entire EHV4 gG gene (1308 nucleotides) plus between 5 and 11 nucleotides upstream from the gG initiation codon and 200 nucleotides downstream from the gG gene (FIGS. 2, 3A and 3B and 6). After digestion of 18S/E with Bam HI and Eco RI, the insert was excised from an agarose gel following electrophoresis, purified using Prep A Gene matrix and buffers (BioRad), and ligated into the Bam HI/Eco RI site of the bacterial expression plasmid pGEX-3X such that the 5'-end of the gG gene was adjacent to and in frame with the 3'-end of the fusion protein glutathione S-transferase (GST). Plasmid pEG4.1 was deposited under the terms of the Budapest Treaty on Oct. 29, 1997, with Australian Government Analytical Laboratories, PO Box 385, Pymble, 2073 Australia, under accession number NM97/11786.

(ii) pEG1.1 contains a 933bp insert encompassing the first 930bp of the EHV1 gG gene plus three base pairs upstream from the initiation codon. This plasmid was derived from an EHV1.438/77 Bam HI D clone utilizing Pst I sites located at either end of the insert, creating blunt ends with Klenow enzyme and dNTP's and ligating into the Sma I site of pGEX-3X.

(iii) pEG1.2 contains the entire EHV1 gG gene of 1,233bp. The insert was derived by polymerase chain reaction (PCR) amplification of the EHV1 gG gene using Vent polymerase (New England Biolabs) at 35 cycles of 94°×20 sec, 48°×20 sec, 72°×2 min. The EHV1.438/77 Bam HI D plasmid which includes the entire gG genc (FIG. 6) was used as template DNA and the synthetic oligonucleotide primers, which encompassed the first and last 17 nucleotides the EHV1 gG gene and included Bam HI sites (in bold type below) plus a 2 base overhang, were as follows: forward 5'-cgggatccatgttgactgtcttagc-3'(SEQ ID NO:8); reverse 5'-cgggatcctaagcaacgtactcaag-3'(SEQ ID NO:9). It was not possible to clone the 1.23 kb PCR product directly into the Bam HI site of pGEX-2T presumably because the Bam HI recognition sites close to the end of the fragment were not readily digested. As a result, the fragment was blunt ended using Klenow DNA polymerase (Pharmacia) and dNTP's followed by phosphorylation using polynucleotide kinase and then cloned into the Sma I site of pUC-19. Digestion of the pUC-19/EHV1 gG clone with Bam HI released the 1.23 kb fragment which was then cloned into the Bam HI site of pGEX-2T.

(iv) pEG4var contains nucleotides encoding EHV4 gG amino acids 287 to 374 and was constructed by PCR amplification (35 cycles of 94°×20 sec, 50°×20 sec, 72°×30 sec) using pEG4.1 DNA as template and the following primers: forward 5'-gaaaatgaaacctacag-3'(SEQ ID NO:10); reverse 5'-tggaggccatgcaacac-3'(SEQ ID NO:11). The fragment obtained was cloned directly into the Sma I site of pGEX-3X. Plasmid pEG4var was deposited under the terms of the Budapest Treaty on Oct. 14, 1997, with Australian Government Analytical Laboratories, PO Box 385, Pymble, 2073 Australia, under accession number NM97/11365.

(v) pEG1var contains the nucleotides encoding EHV1 gG amino acids 288–350 and was constructed by PCR amplification as described above for pEG4var except that EHV1 Bam HI D was used as template DNA and the primers were as follows: forward 5 '-ggtgacgaaacatacga-3'(SEQ ID NO:12); reverse 5'-tggatgccgttcgacgc-3'(SEQ ID NO:13). Plasmid pEG1var was deposited under the terms of the Budapest Treaty on Oct. 14, 1997, with Australian Government Analytical Laboratories, PO Box 385, Pymble, 2073 Australia, under accession number NM97/11366.

GST-fusion protein preparations

The pGEX plasmid was chosen for expression because of the ease with which the GST-fusion protein can be affinity purified by utilizing agarose beads coated with covalently attached reduced glutathione (Sigma), a strong ligand for GST. Several colonies containing the recombinant plasmid were isolated and protein was prepared by a small-scale GST-fusion protein purification method based on that of Smith and Johnson (1988). Briefly, single colonies were inoculated into 5 ml broth cultures and incubated for 4 h at 37° C. after which time 5 $\mu$l of a 1M IPTG stock solution was added and the cultures further incubated for 2 h. The bacteria (1.5 ml of culture) were pelleted by centrifugation at 12,000 g for 2 mins, washed once with 1.5 ml PBS and made up to 0.5 ml with PBS containing 1% Triton X-100. The cells were sonicated at a low setting (2×10 secs) and centrifuged as above. Glutathione agarose beads (75 $\mu$l of a 50% suspension in PBS; Sigma) were then added to the supernatant and the mixture left at 4° C. for 15 mins with intermittent mixing. The beads were centrifuged at 12,000 g for 30 secs, washed 3 times with 1.5 ml of PBS and finally resuspended in 200 $\mu$l of sample buffer prior to SDS-PAGE.

Affinity purification of antibody from selected portions of Western blots

Antibody was affinity purified from selected portions of Western blots by eluting antibody at low pH based on the method of Beall and Mitchell (1986). Briefly, proteins were separated by SDS-PAGE after first loading either EHV4 supernatant, diluted ½ in double strength reducing buffer (200 $\mu$l), or recombinant gG protein (200 $\mu$l) into a 5 cm well. Following the transfer of proteins to PVDF membranes, selected portions of the membranes were cut such that the protein of interest was contained in the cut out portion. To isolate the 63K secreted protein a section containing proteins from 50K–70K was cut out and to isolate the 70K recombinant GST-gG protein a section containing proteins from 65K–75K was cut out. Cut out membrane portions were blocked to prevent non-specific binding by incubating for 1 h in $BSA_5PBST$ containing 5% goat serum.

EHV4 antiserum diluted 1/10 in $BSA_5PBST$ containing 10% goat serum and 10% fetal bovine serum (with total volume of 2 ml) was then added to the cut out membrane for 2 h with constant rocking. The membranes were washed extensively for 30 mins with PBST. Antibody was eluted from each membrane using 2 ml of 0.1M glycine, 0.15M NaCl (pH 2.6) for 3 mins. The eluate was adjusted to pH7.5 by addition of 300 μl Tris-HCl (pH 7.5), diluted 2-fold in $BSA_5PBST$ containing 5% goat serum and either stored at −70° C. or used immediately, with no further dilution, to probe Western blots.

EXAMPLE ONE

Identification of secreted, type-specific glycoprotein(s) of EHV4

EHV4 and EHV1 infected cell culture supernatants were examined for the presence of secreted viral proteins. FIG. 1*a* shows a Western blot of EHV4 infected cell culture supernatant and mock infected cell culture supernatant probed with a pool of post-EHV4 horse sera. An immunodominant region is evident in the EHV4 supernatant at approximately 200K and 63K while no such proteins were seen in the mock supernatant. The supernatant proteins were also probed with a pool of MAbs directed to gp2, gp10, gp14 (large gB subunit) and gp18 (gD) (FIG. 1*a*). Only when the membranes were left in TMB substrate for a prolonged period could these proteins be visualized in the supernatant, indicating that they were all present in low abundance. Nevertheless, gp2 appeared co-migratory with the larger of the secreted products while none of the other three glycoproteins was co-migratory with the 63K secreted product. The small subunit of the gB heterodimer (62K), a major EHV4 glycoprotein which migrates to a position on an SDS-PAGE gel just above gp18 (56K), has a Mr similar to the smaller secreted product (FIG. 1*a*). To examine the relationship between these two proteins and to determine if the secreted products were glycoproteins, [$^{14}$C]glucosamine labelled virion proteins and supernatant proteins were subjected to SDS-PAGE on a large (16 cm×16 cm×0.75 mm), 10% polyacylamide gel (FIG. 1*b*). Glycoproteins at approximately 250K and 63K were evident in the EHV4 supernatant. A small amount of a glycoprotein co-migrating with gp13 was also observed in the EHV4 supernatant suggesting either that this glycoprotein was also secreted, albeit at low levels, or that low levels of all the glycoproteins were present in the infected cell culture supernatant possibly as a result of lysis of some infected cells and that gp13, being the most heavily labelled, was the only glycoprotein easily observed. Both the 250K and 63K products did not appear to exactly co-migrate with viral glycoproteins gp2 and small gB subunit (FIG. 1*b*). Unlike the small gB subunit, the 63K secreted product was identified as a rather diffuse glycoprotein band that did not label particularly well with [$^{14}$C] glucosamine. Furthermore, as the EHV4 gB heterodimer is derived from a single gene and is covalently linked by disulphide bonds, it is unlikely that the small gB subunit would be secreted in the absence of the large gB subunit. It appeared likely, therefore, that both the 250K and 63K secreted products were previously undefined glycoproteins of EHV4.

The type-specificity of the secreted products was exanined. In Western blot the smaller product (63K) was shown to be completely type-specific as it reacted strongly with monospecific horse sera from SPF foals or previously scronegative horses that were either immunized or infected with EHV4 but not with sera from SPF foals that were either immunized or infected with EHV1 (FIG. 1*c*). Of particular note was the seroconversion of foal 2 from a negative to positive reaction in Western blot to the 63K secreted product after this foal, which was initially infected with EHV1 (foal 2a serum), was cross-challenged with EHV4 (foal 2b serum). The 250K secreted product appeared less immunodominant than the 63K secreted product. However, this may be misleading as the 250K secreted product may not have transferred to the PVDF membranes as efficiently as the 63K secreted product.

The ELISA data presented in Table 1 shows that: (a) The monospecific horse sera, mostly obtained from SPF-foals (described above), showed significant ELISA titres of between $10^{3.6}$ (4,000) and $10^{4.3}$ (20,000) when tested against the virus to which they were exposed; either EHV1 or EHV4. (b) Each serum contained antibody which was cross-reactive with the heterologous virus such that its ELISA titre against either virus was very similar. (c) The EHV4 secreted product(s) produced an EHV4 specific response in ELISA i.e., when the EHV4 supernatant was used to coat the wells of ELISA plates post-EHV4 sera showed titres of between 500 and 1000 whereas post-EHV1 sera showed titres of between 20 and 40. This not only confirmed the Western blot results (FIG. 1*c*) but indicated that any discontinuous epitopes on the secreted product(s), that would be presented in this type of assay but not in Western blot, were also type specific; (d) The EHV1 supernatant did not react significantly with any serum indicating that EHV1 did not secrete a protein that was detectable with these immune reagents.

DNA sequence analysis

Figures 2A, 2B, 2C, 2D:
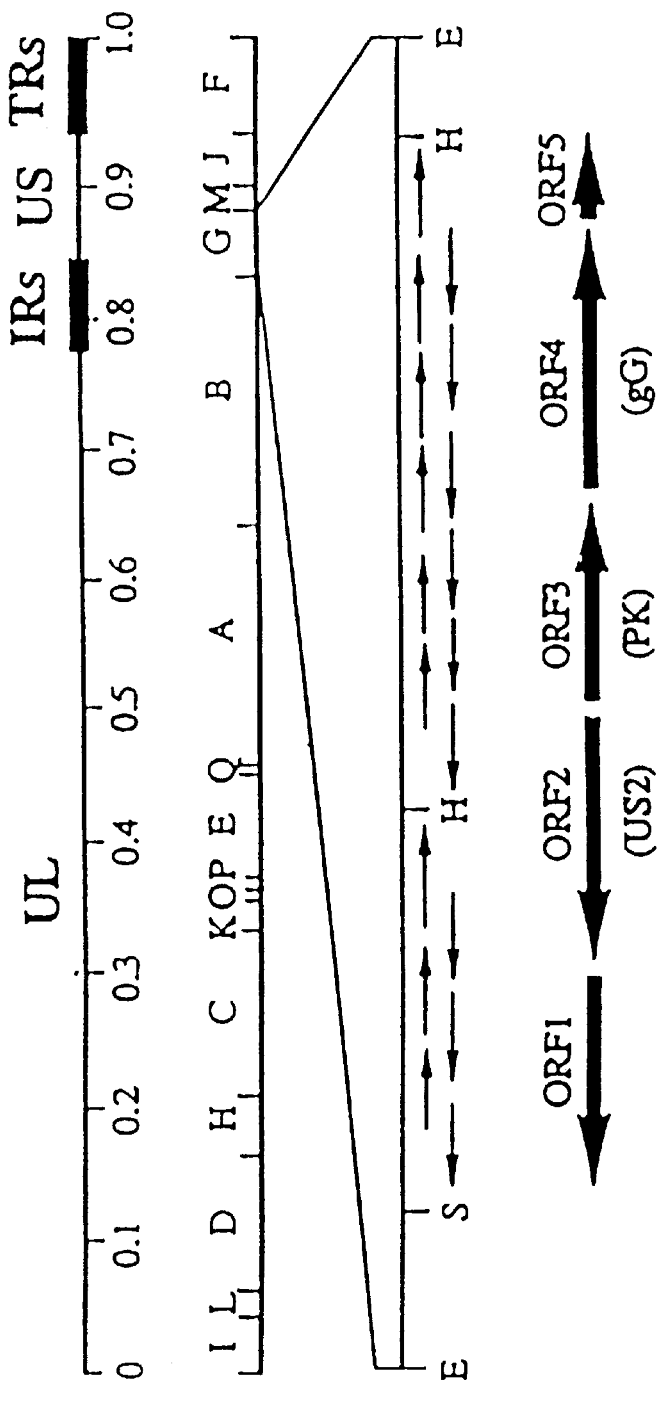
FIG. 2A EHV4 genome showing unique long (UL) and unique short (US) regions as well as the internal and terminal repeat sequences that bracket the US region (IRs and TRs respectively).
FIG. 2B Eco RI retriction endonuclease map of the EHV4 genome.
FIG. 2C Expansion of the Eco RI G fragment showing Sma I (S) and Hind III (H) cleavage sites. The approximate locations of sequences covered by deletion clones are indicated by the arrows.
FIG. 2D Location and orientation of the five major open reading frames (ORFs). The ORFs are given HSV designations (in brackets) if homology was established.

Clones carrying fragments of the US region close to the internal repeat region of the EHV4 genome were sequenced (FIG. 2). Analysis of 5451 nucleotides showed four complete major ORFs, two rightward and two leftward, and one partial ORF in the rightward orientation (FIG. 2). Similarity searches of the GenBank database revealed that ORF2 was most homologous to HSV1 US2, ORF3 to PRV US1 (protein kinase) and its homologue HSV1 US3, ORF4 to PRV US2 (gX), and ORF5 to HSV1 US5 (gJ). No statistically significantly homologous gene was observed for ORF1. Analysis of ORF4, the gene showing similarity to the PRV gX gene, is described below while the other genes are not discussed further in this manuscript.

The sequence of ORF4 and flanking regions is shown in FIGS. 3A and 3B (SEQ ID NOS:1–2, respectively). Examination of the flanking sequences of the ORF4 gene revealed: (a) A TATA box, TATAAA, (bases 33–38 of SEQ ID NO:1) beginning 79 nucleotides upstream from the initiation codon (position -79) aligns well with the PRV gX TATAAA which is at position -65 (Rea et al., 1985) (b) A poly (A) signal AATAAA (bases 1453–1458 of SEQ ID NO:1) located 10 nucleotides downstream from the termination codon (c) A GT-rich region beginning 168 nucleotides downstream from the termination codon.

The coding region comprises 1308 nucleotides coding for 435 amino acids. The N-terminus of the predicted amino acid sequence has some features characteristic of a membrane insertion (signal) sequence including hydrophobic amino acids from Leu-2 to Gly-19 (FIGS. 3A and 3B) followed by a potential peptidase cleavage site between Gly-19 and Arg-20 (FIGS. 3A and 3B). However, there is no positively charged residue(s) to the left of the hydrophobic amino acids which is common for herpesvirus glycoprotein signal sequences. The predicted cleavage site is preceded by a helix breaking residue, Gly-16, which is usual for signal sequences. Further evidence for this location of the cleavage site is shown by comparison of the 9 amino acids of ORF4 which directly follow the predicted cleavage site with the corresponding 9 amino acids of PRV gX, the protein which showed most similarity to ORF4 (see below), in which 6 amino acids directly align including Cys-27 (EHV4) with Cys-28 (PRV). The C-terminal 18 amino acids are hydrophobic in nature and this region may comprise the glycoprotein transmembrane domain (FIGS. 3A and 3B). The sequence contains 5 potential asparagine-liinked (N-linked) glycosylation sites, which require the motiff Asn-X-Ser/Thr where X is not a proline residue, occurring at positions 83, 138, 174, 221 and 288 (FIGS. 3A and 3B).

Only two proteins in the GenPept protein database showed significant identity with the predicted amino acid sequence of ORF4, PRV gX (the HSV gG homologue) and HSV2 gG. ORF4 showed 28% overall amino acid identity with PRV gX although significantly greater identity was apparent toward the N-terminus. The similarity of the two sequences was further evidenced by the conservation of 5 cysteine residues, 4 located in the N-terminal region, and by the occurrence of 8 separate regions of 4 to 6 identical residues. There was also a limited identity (16%) observed between ORF4 and HSV2 gG but again greater identity was observed toward the N-terminus including conservation of the same 4 cysteine residues as conserved with PRV gX. The EHV4 gG N-linked glycosylation site at position 138 was conserved in both PRV gX and HSV2 gG, suggesting that this site at least is probably utilized, while those at positions 83 and 221 were conserved in PRV gX only. On a basis of the similarity observed between ORF4 with PRV pX and with HSV2 gG, ORF4 was designated EHV4 gG.

Expression of the EHV4 gG gene to identify 63K secreted product as EHV4 gG

Figures 4A, 4B:
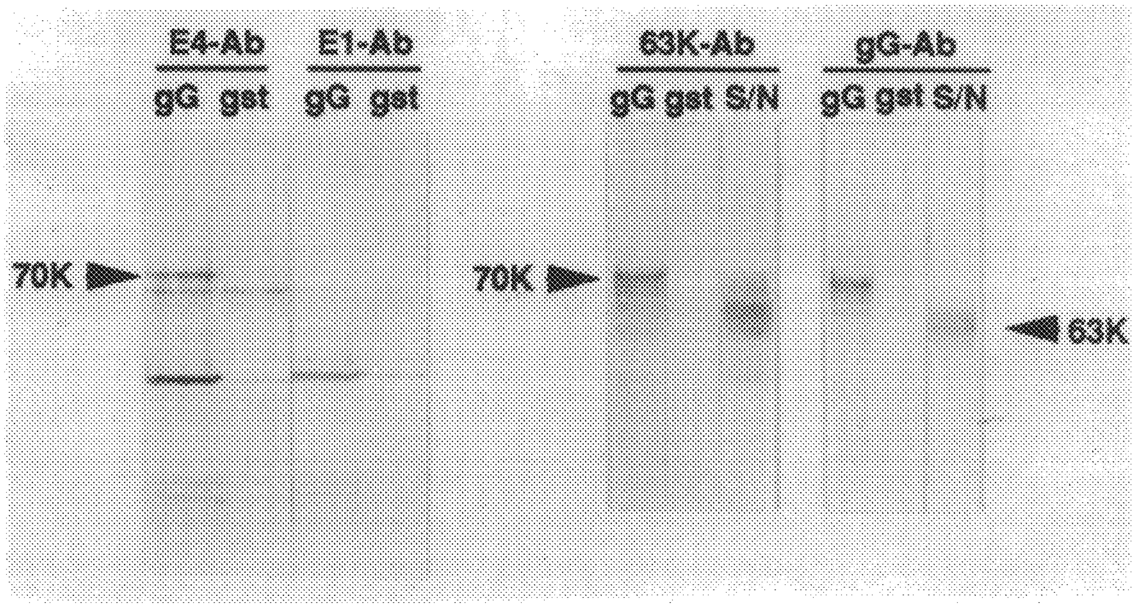
FIG. 4A Western blots of EHV4 glycoprotein G-glutathione S-transferase fusion protein (gG) which was produced in *E. coli* transformed with a EHV4 gG pGEX-3X recombinant plasmid and prepared by purification using glutathione-agarose beads. GST only (gst) was included as a control and was prepared by transformation of *E. coli* with parental plasmid pGEX. The PVDF membranes were probed with either a pool of post-EHV4 sera (E4-Ab) which included sera from an SPF foal immunized with EHV4 (SPF foal 3) and a previously seronegative horse that was experimentally infected with EHV4 (post-EHV4 infection horse 2) or a pool of post-EHV1 sera (E1-Ab) which included sera from SPF foals that were either immunized (SPF foal 1) or experimentally infected with EHV1 (SPF foal 2a). The 70K gG-GST fusion protein is arrowed.
FIG. 4B Western blots of gG-GST fusion protein (gG), GST only (gst) and EHV4 secreted proteins derived from the supernatant of EHV4 infected cell cultures (S/N) probed with antibody from post-EHV4 infection horse 2 that had been affinity purified from selected portions of Western blots that contained either the gG-GST fusion protein (gG-Ab) or the 63K EHV4 secreted protein (63K-Ab). The 70K gG-GST fusion protein and the 63K secreted protein are arrowed.

A 1.5 kilobase pair subfragment which contained the entire gG gene (1308 base pairs) as well as five base pairs upstream and 200 base pairs downstream of the gG gene was cloned into pGEX-3X ensuring that the gG gene was in frame with the GST fusion protein gene. The resulting pGEX-EHV4-gG recombinant clone was termed pEG4.1. The fusion protein subsequently expressed by pEG4.1 transformed cells was, after purification on glutathione-agarose beads, identified in Western blot using a pool of post-EHV4 horse sera (FIG. 4*a*). This protein had a Mr of 70K; the gG portion constitutes 43K as the Mr of GST is 27K. The 70K fusion protein did not react in Western blot with a pool of post-EHV1 SPF-foal sera (FIG. 4*a*). A corresponding band was not observed in the control preparations from cells transformed with pGEX only.

To determine if the EHV4 63K secreted product described earlier was in fact gG, antibody was affinity purified from selected portions of Western blots that contained either the 63K secreted product or the 70K EHV4 GST-gG fusion protein. Using these two affinity purified antibody preparations to probe Western blots it was shown that both antibody preparations reacted strongly with the 63K EHV4 secreted product and the 70K EHV4 gG fusion protein (FIG. 4*b*). This confirmed that gG was the 63K product found in the cell culture medium of infected cells. It was also apparent that the 250K secreted product was not related to the 63K secreted product as neither antibody preparation reacted with this glycoprotein (FIG. 4*b*). A glycoprotein at 63K was also detected on Western blots of purified EHV4 virions using both affinity purified antibody preparations (data not shown).

Comparison of the sequences of EHV4 gG and EHV1 gG.

The nucleotide sequences of EHV1 gG from two different strains, EHV1.Ab4p, and EHV1.KyA, and the EHV4 gG sequence of strain EHV4.405/76 (described here) and have not been compared. The two EHV1 gG sequences differed from each other in three nucleotides all located toward the 3'-terminus of the gene and all resulting in frame shifts (data not shown). A missing guanosine at the first position of codon 335 in EHV1.KyA gG results in a different codon usage from EHV1.Ab4p gG until an additional adenosine in EHV1.KyA gG at the first position of codon 356 restores the two sequences to identical codon usage. Also, a missing cytidine at the third position of codon 374 in EHV1.KyA gG produces a stop codon whereas EHV1.Ab4p gG reads to codon 411. Therefore the two published sequences of EHV1 gG not only differ in their amino acids at positions 335–356 but are of different lengths with EHV1.KyA gG possessing 373 and EHV1.Ab4p gG 411 amino acids.

In an attempt to reconcile these differences we determined the nucleotide sequence of the 5'- and 3'-termini (approximately 300 nucleotides at each end) of recombinant plasmid pEG1.2 which contains the entire EHV1 gG gene derived from our prototype EHV1 strain 438/77 (data not shown). T1 he sequence obtained, which covered all the ambiguous nucleotides, was identical to that of the EHV1.Ab4p gG sequence. Furthermore, the size of the GST-fusion protein produced by pEG1.2 (72K) was slightly larger than the GST-fusion protein produced by pEG4.1 (70K), an expression plasmid containing the entire EHV4.405/76 gG gene which codes for a protein of 435 amino acids (FIGS. 3A and 3B). This is consistent with EHV1.438/77 gG, like its EHV1.Ab4p counterpart, comprising 411 amino acids.

Figure 5B:
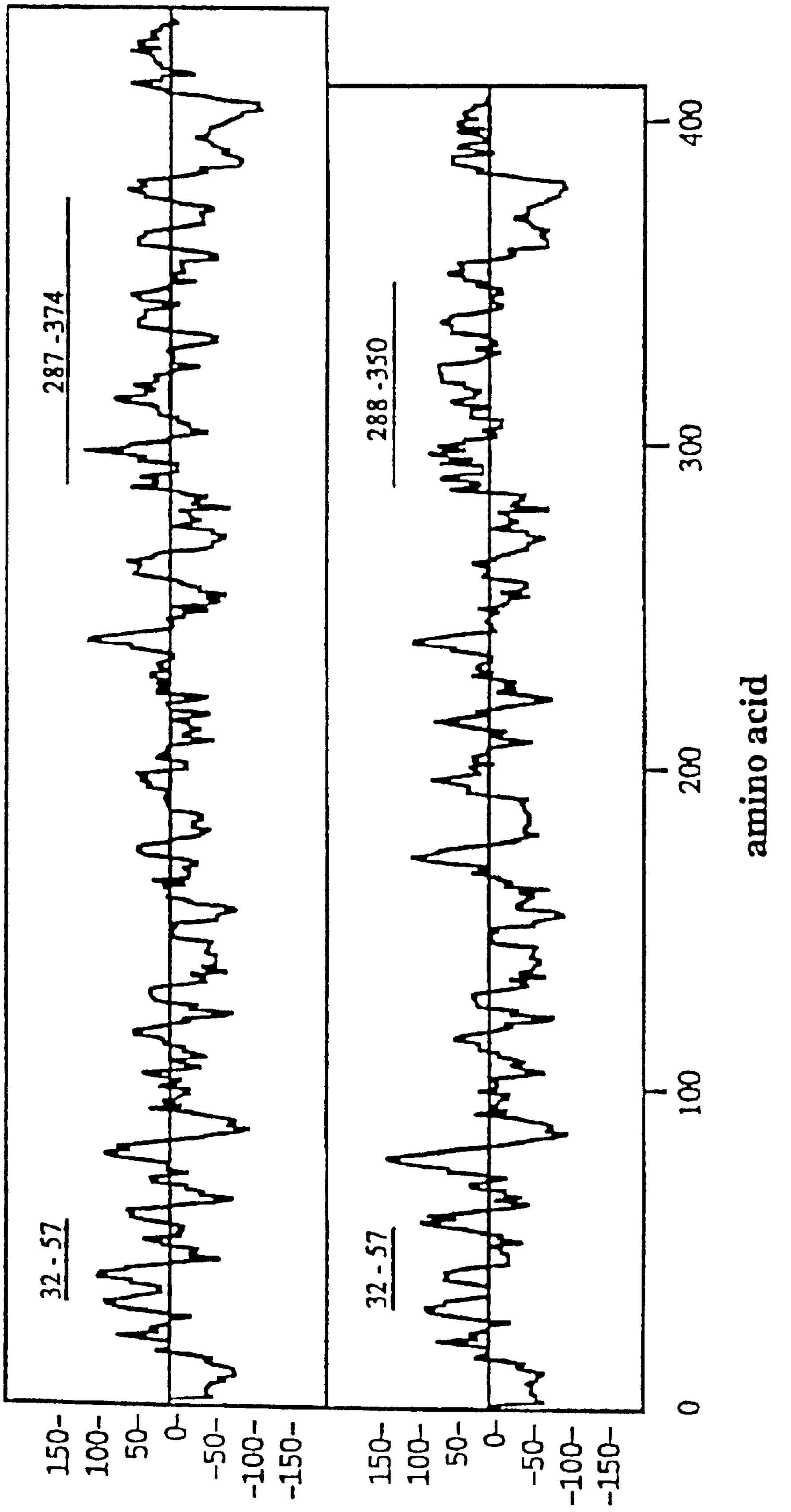
FIG. 5B Hydropathic analysis of EHV4 gG (top panel) and EHV1 gG (bottom panel) amino acids according to the algorithm by Hopp and Woods (28). The X-axis represents the amino acid number and the Y-axis considered hydrophilic and likely to comprise antigenic sites. The most variable regions of the two sequences are overlined and the amino acid numbers shown.

A comparison of the predicted amino acid sequences of EHV4.405/76 gG and EHV1.Ab4p gG is shown in FIG. 5*a* (SEQ ID NO:2–3, respectively). These glycoproteins show an overall identity of 58% with the C-terminal region generally showing considerably more divergence than the N-terminal region. Amino acids 1–286 of EHV4 gG and 1–287 of EHV1 gG show an identity of 75% whereas the apparently corresponding C-terminal regions of EHV4 gG, amino acids 287–374, and EHV1 gG, amino acids 288–350, have diverged widely and exhibit little amino acid identity (FIG. 5*a*). Another region of considerable diversity is a 25 amino acid region, residues 32–57 of both viruses, in which only 9 amino acids (36%) are identical. The nucleotide sequences of EHV4 gG and EHV1 gG also show considerable divergence in the two above mentioned variable regions (data not shown). Using the protein algorithm of Hopp and Woods both divergent regions are predicted to encompass antigenic sites (FIG. 5*b*).

EHV4 gG and EHV1 gG each has 9 cysteine residues in their respective predicted extracellular domains all which are conserved between the two viruses. Four cysteine residues located toward the N-terminus are conserved with pseudorabies virus (PRV) gG (gx), HSV2 gG and infectious laryngotracheitis virus (ILTV) gG (gX) (FIG. 5*a*). The predicted extracellular domain also contains five and six potential N-linked glycosylation sites for EHV4 gG and EHV1 gG respectively. The three N-linked glycosylation sites at positions 83, 138 and 221/222 (EHV4/EHV1) that are conserved between EHV4 gG and EHV1 gG are also conserved in PRV gG (gX) while the site at position 138 is also conserved in HSV2 gG and ILTV gG (gX) (FIG. 5*a*).

The C-terminal variable region of EHV4 gG (SEQ ID NO:2) (amino acids 287–374) also possesses a repeated sequence of 9 amino acids MKNNPXYSE, where X is an isoleucine in the first repeat and a valine in the second, which is separated by 18 amino acids (FIG. 5*a*).

Expression of EHV4 gG- and EHV1 gG-fusion proteins (SEQ ID NOS:2–3, respectively).

Figure 6A:
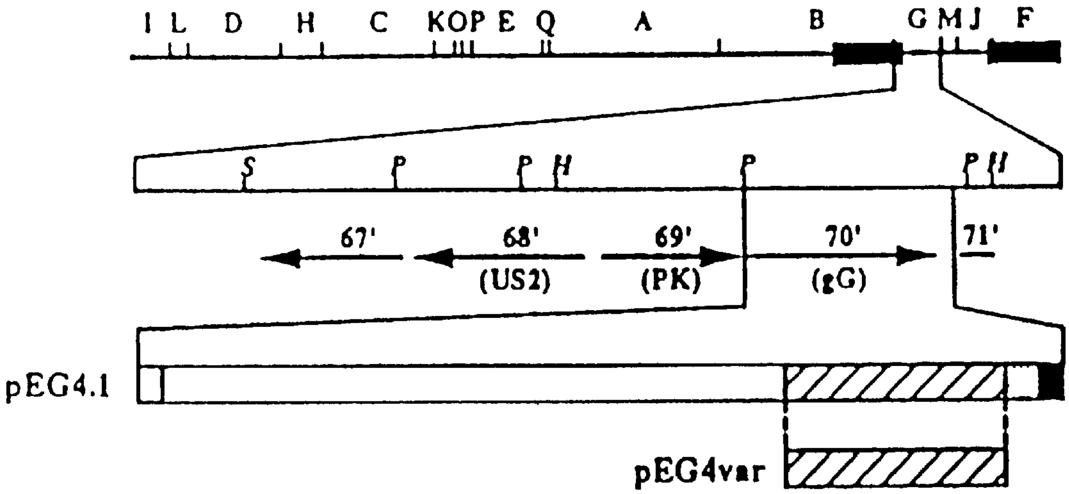
FIG. 6 Strategy for cloning EHV4 gG FIG. 6(A) and EHV1 gG FIG. 6(B). The Eco RI restriction endonuclease map of the EHV4 genome and the Bam HI restriction endonuclease map of the EHV1 genome are shown at the top of FIGS. 6A and B respectively. The Eco RI G fragment of the EHV4 genome and the Bam HI D fragment of the EHV1 genome are expanded. Sma I (S), Hind III (H) and Pst I (P) cleavage sites are indicated for EHV4 Eco RI G while Pst I (P) cleavage sites are indicated for EHV1 Bam HI D. The location and orientation of the known open reading frames contained within these fragments are indicated by the arrows. The EHV1 ORFs are numbered according to the designations of Telford et al while their EHV4 homologues are given the same numbers but distinguished using a prime. HSV designations are given (in brackets) if homology has been established. The bottom of each panel shows a schematic representation of the various gG molecules expressed by the recombinant plasmids pEG4.1 and pEG4var FIG. 6(A) and pEG1.1, pEG1.2 and pEG1var FIG. 6(B). Predicted signal sequences and transmembrane domains are indicated by the open and closed boxes respectively and the C-terminal variable regions of EHV4 gG (amino acids 287–374) and EHV1 gG (amino acids 288–350) are shown by the cross-hatching.
Figure 6B:
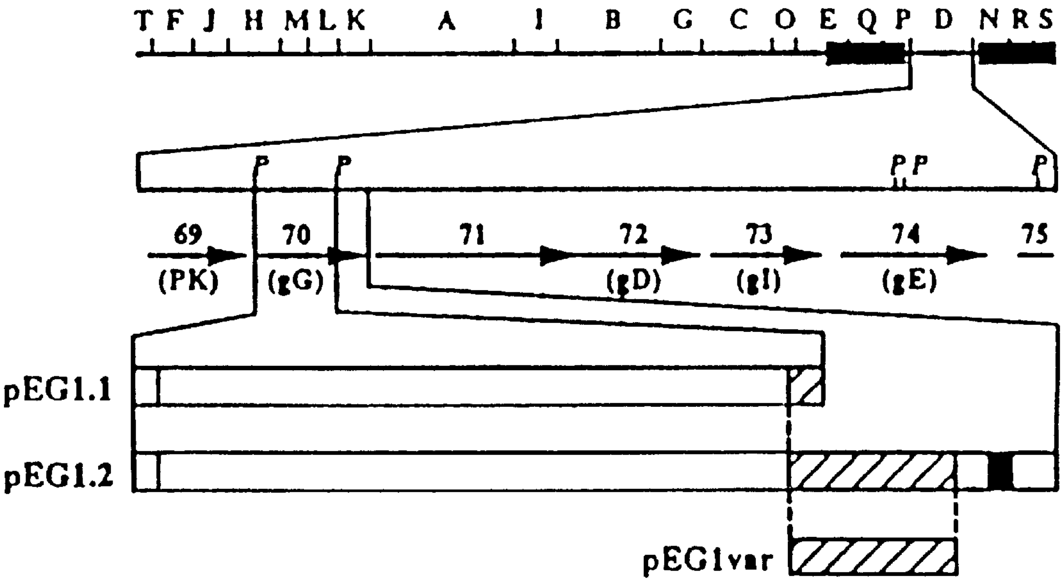
Figure 7:
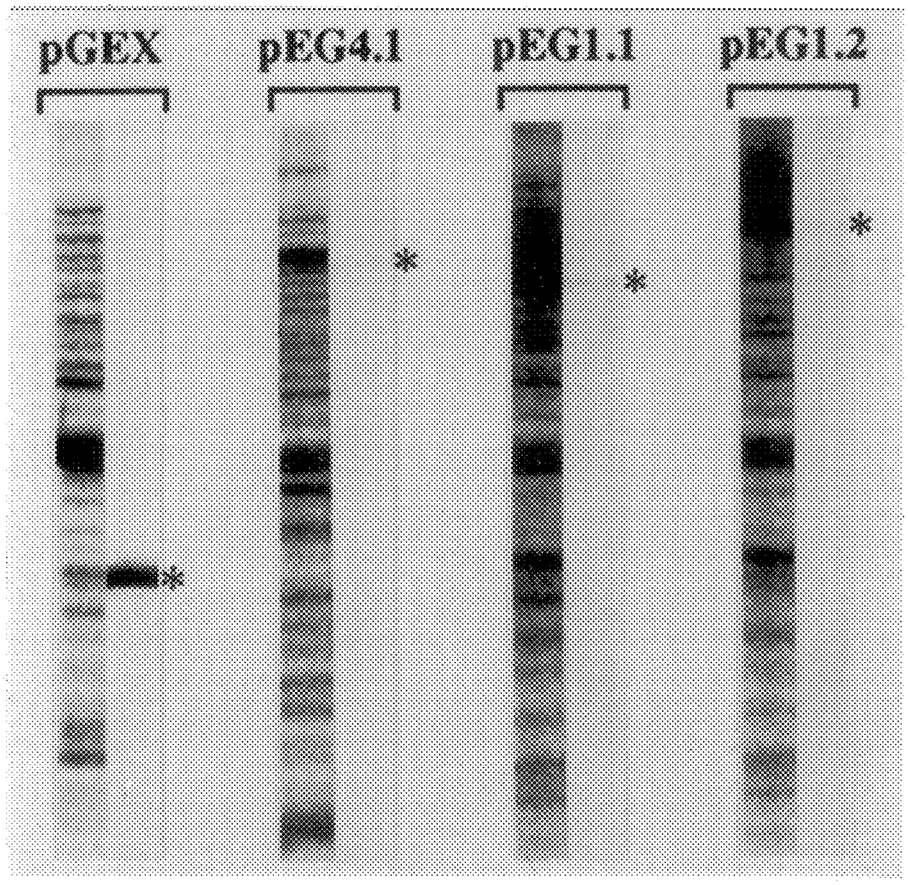
FIG. 7 Coomassie brilliant blue staining of GST-gG fusion proteins expressed in *E. coli* transformed with parental pGEX, pEG4.1, pEG1.1 or pEG1.2 following SDS-PAGE. Two samples were prepared for each clone comprising the pellet remaining after solubilization of the *E. coli* (left strip) and the purified GST-fusion protein (right strip). The location of the GST-fusion proteins at 27K (pGEX), 70K (pEG4.1), 60K (pEG1.1) and 72K (pEG1.2) are indicated by the asterisks.
Figure 8:
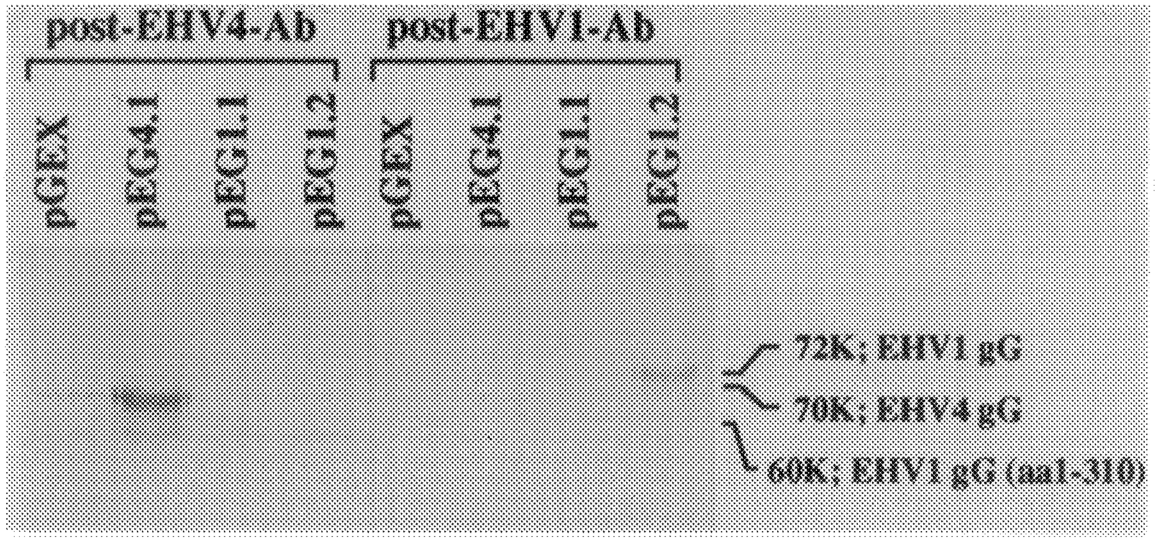
FIG. 8 Western blot of GST-gG fusion proteins expressed in *E. coli* transformed with parental pGEX, pEG4.1, pEG1.1 or pEG1.2. Membranes were probed with pooled SPF foal 3 and post-EHV4 No.2 horse sera (post-EHV4-Ab) or pooled SPF foal 1 and SPF foal 2a horse sera (post-EHV1-Ab). All samples were run on the same SDS-PAGE gel. Approximate Mr values of GST-gG fusion proteins produced by pEG4.1 (EHV4 gG), pEG1.1 (EHV1 gG (aa1-310)) or pEG1.2 (EHV1 gG) are indicated to the right.

*E. coli* transformed with recombinant pGEX plasmids pEG4.1, pEG1.1 or pEG1.2 express GST-fusion proteins associated with either entire EHV4 gG (435 amino acids), partial EHV1 gG (amino acids 1–310) or entire EHV1 gG (411 amino acids) respectively (FIGS. 6, 7 and 8). The fusion proteins were purified and assessed for their capacity to bind to antibody in pools of post-EHV4 only or post-EHV1 only horse sera (FIGS. 7 and 8; Table 2). It was evident from Coomassie Brilliant Blue staincd SDS-PAGE gels that pEG4.1, pEG1.1 and pEG1.2 produced stable fusion proteins of approximately 70K, 60K and 72K respectively (FIG. 7). However, unlike GST alone these recombinant GST-fusion proteins were largely insoluble and remained in the cell pellet after solubilization (FIG. 7). Nevertheless, adequate amounts of the fusion proteins were purified for Western blot analysis. Pooled post-EHV4 only horse sera reacted strongly with pEG4.1 fusion protein but not with pEG1.1 or pEG1.2 fusion proteins (FIG. 8). Conversely, pooled post-EHV1 only horse sera showed strong reactivity with pEG1.2 but not with pEG1.1 or pEG4.1. Therefore, it was apparent that EHV4 gG- and EHV1 gG-fusion proteins possessed strong type-specific, presumably continuous epitope(s). It also appeared as though these epitope(s) were located in the C-terminal regions of the glycoproteins as pEG1.1, which expressed amino acids 1–310 of EHV1 gG, was not antigenic whereas pEG1.2, which expressed amino acids 1–411 of the same protein, was a strong antigen. The insolubility of pEG4.1, pEG1.1 and pEG1.2 fusion proteins meant that relatively large amounts (approximately 50 $\mu$l (¼) of one small-scale fusion protein preparation) of purified GST-fusion protein was required. As a result some contaminating *E. coli* protein bands were evident in the Western blot shown in FIG. 8.

Figure 9:
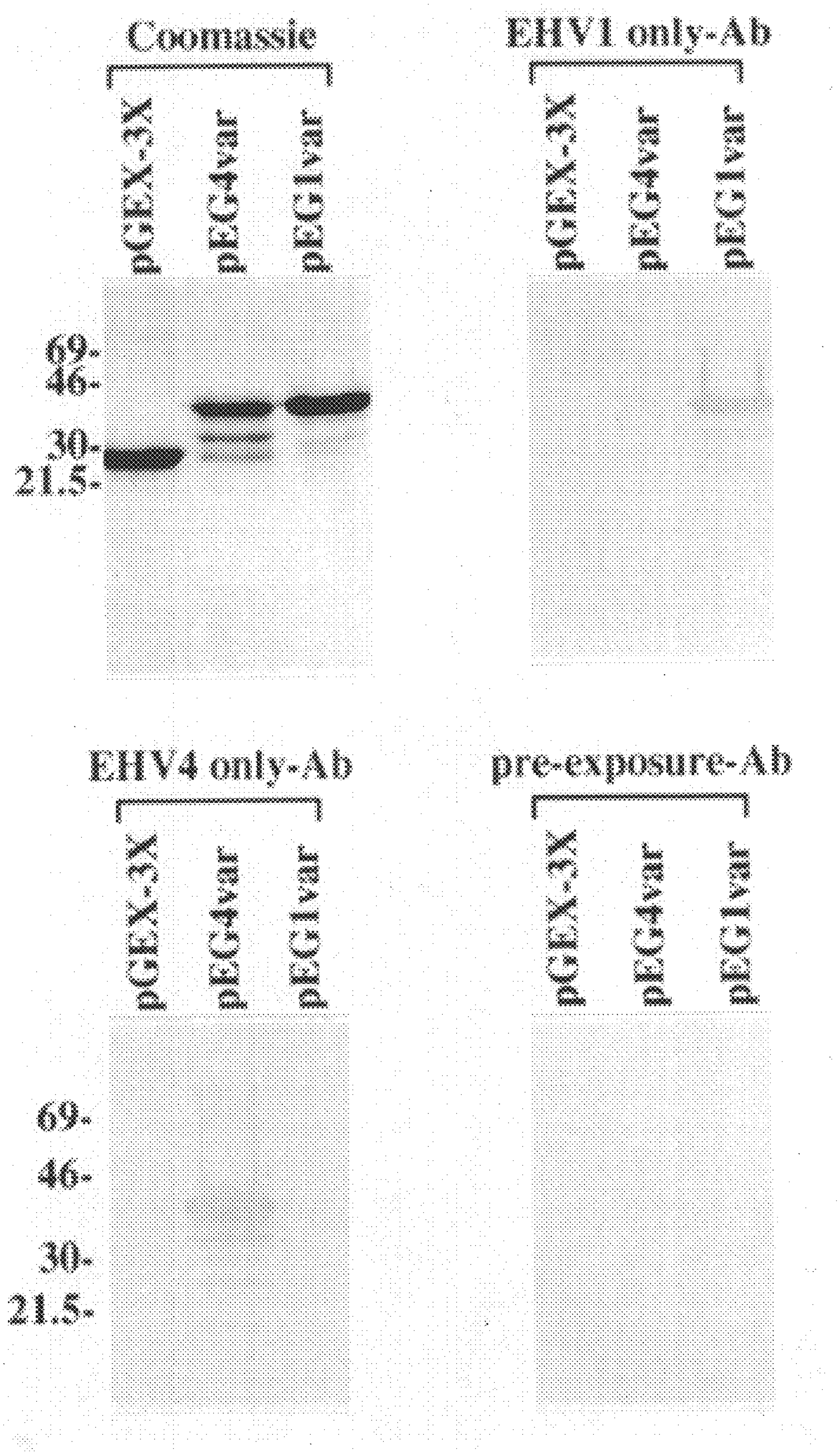
FIG. 9 Coomassie brilliant blue (Coomassie) and Western blot of GST-gG fusion proteins expressed in *E. coli* transformed with parental pGEX, pEG4var or pEG1var. Membranes were probed with pooled SPF foal 3 and post-EHV4 No.2 horse sera (EHV4 only-Ab) or pooled SPF foal 1 and SPF foal 2a horse sera (EHV1 only-Ab) and pooled SPF foal preexposure sera (preexposure-Ab). Approximate Mr values of GST fusion proteins produced by pGEX (GST only), pEG4var (E4 gG aa 287–374) or pEG1var (E1 gG aa288–350) are indicated to the right. 1 μm gm of fusion protein was loaded to each lane.

It was considered most likely that these type-specific, continuous epitope(s) were located in the C-terminal variable regions of EHV4 gG (amino acids 287–374) and EHV1 gG (amino acids 288–350). To show this as well as to produce more soluble antigens that are able to be purified in large amounts two pGEX-3X clones, termed pEG4var and pEG1var, which express the corresponding variable regions of EHV4 gG and EHV1 gG respectively were constructed. The GST-gG fusion proteins produced by pEG4var and pEGlvar were highly soluble as reflected by the ease of purification from *E. coli* lysates (FIG. 9). These antigens were also strongly type-specific in Western blot using pooled post-EHV4 only or post-EHV1 only horse sera thereby confirming that the location of type-specific epitopes was within these variable regions (FIG. 9).

Figure 10:
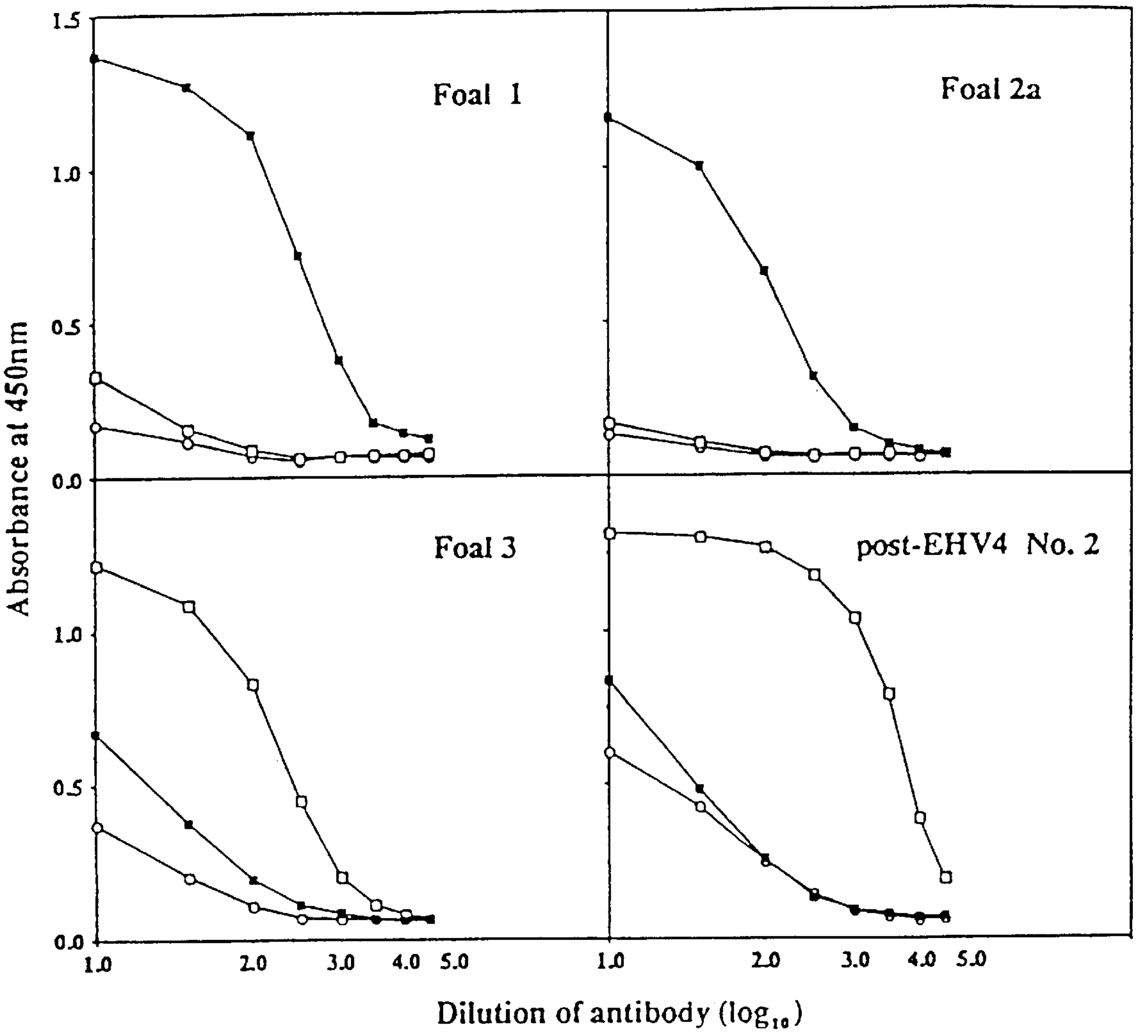
FIG. 10 Titration curves showing reactivity in ELISA of SPF foal 1, SPF foal 2a, SPF foal 3 and post-EHV4 No.2 horse sera with the recombinant proteins GST only (open circles), GST-EHV4 gG (amino acids 287–374; open squares) and GST-EHV1 gG (amino acids 288–350; closed squares) produced by *E. coli* transformed with pGEX, pGE4var, or pEG1var respectively.

An ELISA was developed using the recombinant gG antigens produced by pEG4var and pEG1var. FIG. 10 shows the titration curves obtained for the four polyclonal horse sera used as the pooled sera to produce the Western blots described above. Post-EHV4 only (foal 3 and post-EHV4 No. 2) or post-EHV1 only (foal 1 and foal 2a) horse sera showed a type-specific serological response against the GST-EHV4 gG or -EHV1 gG fusion proteins respectively. The slight reactivity observed at low dilutions for foal 3 and post-EHV4 No. 2 sera against GST-EHV1 gG and GST-only was probably due to reactivity against contaminating *E. coli* proteins which would be present at low (and variable) levels in the antigen preparations as no cross-reactivity was observed for these sera with GST-EHV1 gG or GST-only in Western blot (FIG. 9).

Several other horse sera were tested in ELISA for reactivity to the GST-gG fusion proteins produced by pEG4var or pEG1var and the titres obtained are shown in Table 2. From the data shown in Table 2 it was evident that: (a) The post-EHV4 or post-EHV1 only horse sera showed significant ELISA titres of between 4,000 and 21,000 when tested against the virus to which the horses were exposed. (b) Each serum contained antibody which was cross-reactive with the heterologous whole virus such that its ELISA titer against either virus was very similar. (c) The GST-EHV4 gG and -EHV1 gG fusion proteins reacted type-specifically against all the known post-EHV4 only and post-EHV1 only sera tested; low levels of cross-reactivity were not significantly different from the reactivity to GST-only. (d) SPF foal 2, which was initially experimentally infected with EHV1 (foal 2a serum) and consequently reacted against GST-EHV1 gG only , seroconverted after cross challenge with EHV4 (foal 2b serum) to become reactive against both GST-EHV4 gG and GST-EHV1 gG. It was also noted that cross-challenge with EHV4 did not boost the response to GST-EHV1 gG, indeed antibody to GST-EHV1 gG actually showed a 4-fold decrease. (e) The two post-EHV1 abortion mare sera, which were obtained 5 weeks (abortion mare 1) and one year (abortion mare 2) after abortion, reacted strongly against both GST-EHV1 gG and GST-EHV4 gG. (f) Exposure to different virus strains of EHV4 and EHV1 did not affect the serological response to their respective GST-gG antigens, which is particularly relevant in the case of EHV1.849/89 which was isolated from abortion mare 2 and which is an intratypic variant EHV1.1B electropherotype As can be seen from the above description, examination of the supernatant of EHV4 infected cell cultures revealed the presence of two previously unidentified, secreted glycoproteins, one at 250K and the other at 63K. The 63K product was shown to unexpectedly elicit a type-specific antibody response in the horse, the first EHV4 or EHV1 antigen known to produce such a response. There were two lines of evidence suggesting the 63K secreted product may be the EHV4 homologue of HSV gG: (a) gG homologues in PRV and HSV2 are also, at least in part, secreted into the cell culture medium and (b) gG homologues of other herpesviruses have proved to be relatively divergent glycoproteins and therefore perhaps more likely to produce a type-specific antibody response than other glycoproteins. These data led us to sequence the US region of the EHV4 genome adjacent to the internal repeat structure, the location of gG homologues in PRV, HSV1 and HSV2.

The nucleotide sequence of four complete ORFs and one partial ORF were determined: ORF1 for which no homologue was found, ORF2 which showed similarity to HSV1 US2 which codes for an as yet unidentified protein, ORF3 which showed similarity to PRV US1 and HSV1 US3 genes which code in both cases for a protein kinase and ORF4 which showed most similarity to PRV US2 which codes for gX, the homologue of HSV gG. Although the predicted amino acid sequence of ORF4 showed only 28% and 16% identity PRV gX and HSV2 gG respectively, significantly greater identity was apparent toward the N-terminus including the conservation of 4 cysteine residues across the three glycoproteins. PRV gX and HSV2 gG were the only two sequences in the GenPept database to show significant similarity to ORF4. This gene was, therefore, considered to code for EHV4 gG.

Evidence is accumulating that glycoprotein G homologues have some unusual features not found in other alphaherpesvirus glycoproteins. Perhaps the most striking of these is their considerable heterogeneity, particularly toward the C-terminus of the molecules. It is apparent that the genes have diverged widely both by point mutation and by the deletion and/or insertion of segments of DNA. HSV1 gG in particular appears to have suffered a large internal deletion. Consequently the sizes of the predicted amino acids sequences are widely disparate compared to other alphaherpesvirus glycoprotein gene homologues; HSV1 gG comprises 238 amino acids, HSV2 gG 699, PRV gG (gX) 498, EHV4 gG 405, EHV1 gG 411 and ILTV gG (gX) 298.

The gG homologues of EHV4 and EHV1 show only 58% amino acid identity; considerably less than the next most divergent of the sequenced EHV4/EHV1 glycoproteins, gC, which shows 79% identity and which possess both shared and unique epitopes. It is perhaps not surprising then that EHV4 gG and EHV1 gG have proved to be the only EHV4/EHV1 antigens that are type-specific. Significantly, the epitopes responsible for eliciting a strong type-specific response in the natural host are localized to the apparently corresponding, C-terminal variable regions of EHV4 gG (amino acids 287–374) and EHV1 gG (amino acids 288–350), regions which appear to have few constraints on either the number or type of amino acid except perhaps that the amino acids in this region tend to be hydrophilic. Discontinuous epitopes, that are probably not formed in the *E. coli* expressed products, may be present on native gG molecules. Indeed another variable region comprising amino acids 32–57 of both EHV4 gG and EHV1 gG, which does not appear to be antigenic in the *E. coli* expressed molecules, may comprises part of a discontinuous epitope. Such epitopes are largely type-specific since secreted EHV4 gG, as present in cell culture supernatant, reacts type-specifically with polyclonal horse sera in ELISA.

Another feature of the gG homologues is that all, except HSV1 gG and EHV1 gG, have been shown to be secreted, at least in part, into the growth medium. HSV1 gG does not appear to be secreted and this is probably due to a large internal deletion which results in the loss of the proteolytic cleavage site. In the case of EHV1 gG, a secreted protein has not been detected in the infected cell culture supernatants from several different strains of EHV1 using ELISA or Western blot analyses. This does not mean, however, that a secreted form of EHV1 gG, does not exist. It is possible, as is predicted to be the case with EHV4 gG, that the protcolytic cleavage Site is located within the C-terminal variable region, amino acids 288–350; a region which possesses a strong, perhaps the immunodominant, epitope(s). Proteolytic cleavage of EHV1 gG may either destroy such an epitope(s) or leave the epitope(s) present in the virion associated species such that the secreted species does not possess any strong epitopes easily detectable in ELISA or Western blot. The complete lack of reactivity of an EHV1 gG fusion protein expressing amino acids 1–310, which includes some of the variable region, lends some support to such a proposal.

Application of glycoprotein G to a diagnostic test and vaccine development.

The overall rational and methods for diagnostic testing and vaccine development used in the instant invention are well documented in the art and shall not be repeated in the instant specification. For example:

Australian Patent 591145, U.S. Pat. No. 5,041536, and WO 92/21751 disclose diagnostic kits, test methods and vaccination utilizing single virus types. Such methodology is generally applicable to the instant invention and the above documents are incorporated by herein reference.

WO 90/13652 and WO 90/13573 disclose diagnostic kits, test methods and vaccination utilizing dual virus types having a broad divergence. Such methodology is generally applicable to the instant invention and the above documents are herein incorporated by reference.

However, the instant invention differs from the specific disclosures above by allowing, for the first time, the diagnosis and selective treatment of two very closely related viruses which up until recently have remained virtually indistinguishable.

It is evident since EHV4 gG and EHV1 gG are type specific, that the genes coding for these glycoprotein could be deleted using recombinant DNA techniques from vaccine strains of the two viruses such as that developed based on EHV4.405/76 and as described in U.S. Pat. No. 5,084,271 although any strain of EHV4 or EHV1 could be used. The deletion of the genes for gG would mean that a horse immunized with such vaccines would not make antibodies to the gGs, whereas a horse infected with wild type EHV4 and/or EHV1 i.e., viruses containing the gene coding for gG, would make such antibodies. In this way horses immunized with a gG deletion mutant virus vaccine could be distinguished from horses infected or immunized with a gG containing virus.

The data obtained since the priority date for EHV4 gG as presented herein confirms directly that EHV1 gG is type specific, and that EHV1 vaccine with a deleted gG gene would not produce antibodies to gG when administered to a horse, and that therefore a lorse immunized with an EHV1 gG deletion mutant virus can be distinguished from a horse infected with wild type EHV1 i.e., a strain containing an intact gG gene.

Accordingly not only does an immunological test where an enzyme linked immunosorbent assay (ELISA), in which EHV4 gG and EHV1 gG are used as the antigens to distinguish horses that have been infected with either EHV4 or EHV1 or both viruses, the same test in a somewhat modified format can be used to distinguish horses that have been immunized with EHV4 or EHV1 or combined vaccines to both viruses in which the individual viruses i.e., EHV4 and EHV1, contain a deletion in the gG gene.

Figure 11:
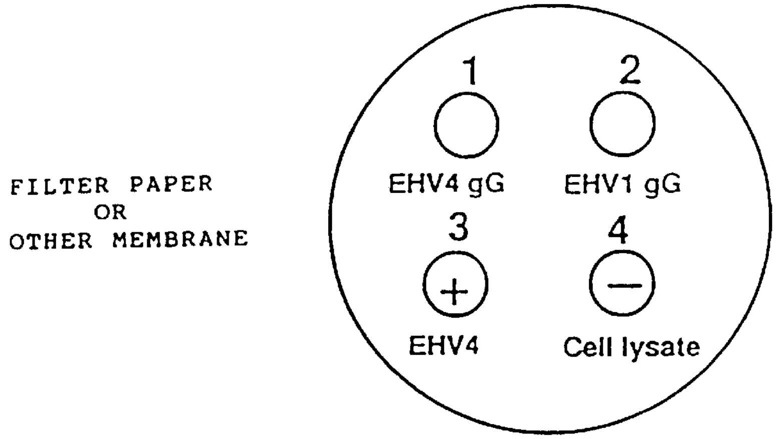
FIG. 11 The four numbered circles are spots on the filter paper impregnated with the designated antigen. In this format a horse immunized with an EHV4 and/or EHV1 gG gene deleted virus would not contain antibody to either gG so there would be no colour change in the upper two dots. However, the horse would contain antibody to many (all) other antigens of EHV4 and EHV1 and hence the lower left whole EHV4 (or EHV1) spot would give a colour change-indicative of a vaccinated but not an infected horse. An example of this type of test is marketed by Agritech Systems Inc under the trade mark "CITE".
Figure 12:
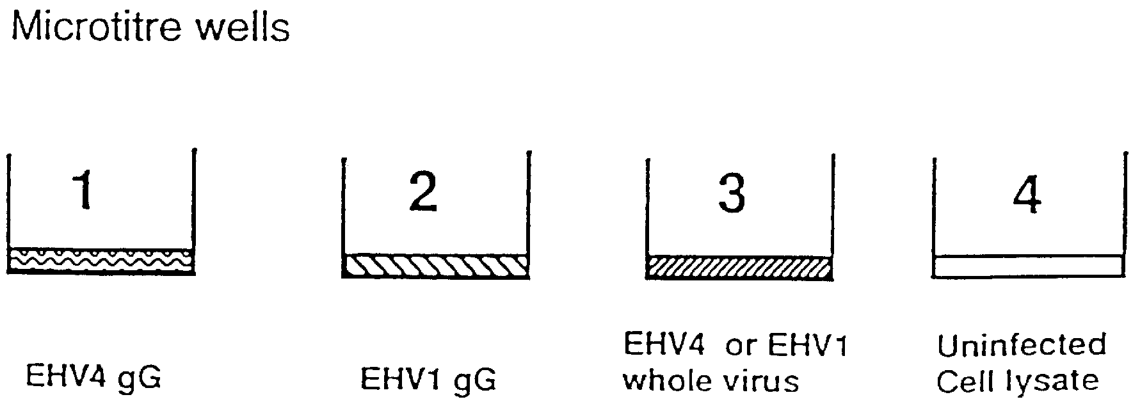
FIG. 12 This test could also be formatted in, for example, the familiar 96-well microprocedure plate (four wells of which are represented) in which alternate triplet wells would contain EHV4 gG, EHV1 gG and either EHV4 or EHV1 whole virus absorbed to the bottom of the well. Appropriate other negative and positive control wells or spots, in the case of the filter paper test, could be included to further validate the test. The fourth well shown contains an uninfected cell lysate as an example of a negative control. An example of this type of test is marketed by Agritech Systems Inc under the trade mark "PETCHEK".

FIGS. 11 and 12 suggest some of the many possible formats for the ELISA test kits that can be used. In FIG. 12 it is shown that antibody obtained in horse serum is first added to the filter paper disc and allowed to react with the designated impregnated antigens. Following washing a second anti-species antibody, such as goat anti-horse IgG antibody, that is conjugated to an enzyme is added to the filter paper and allowed to react with any bound horse antibody. After further washing substrate to the enzyme is added. If EHV4 gG and/or EHV1 gG antibody is present in the serum the EHV4 gG and/or EHV1 gG spot will show a colour change, indicating the horse has been infected with EHV4 and/or EHV1 or immunized with EHV4 and/or EHV1 strains containing the gG gene. If the horse has been infected with both viruses, both gG spots will show a colour change and if the horse has been infected with neither virus neither spot will show a colour change. The test procedure and rationale as disclosed in the FIV test product, CITE®, is incorporated by reference.

As illustrated in FIG. 12, the test can equally be formatted in familiar 96-well microprocedure trays in which the gG antigens to EHV4 (well 1) and EHV1 (well 2) are coated onto the bottom of alternate wells in the tray. Such a 96-well format, which includes appropriate control wells, such as whole EHV4 or EHV1 virus (well 3) and uninfected cell lysate (well 4), is suitable for mass screening of serums from large horse populations. The test procedure and rationale as disclosed in the FIV test product, PETCHEK®, is incorporated herein by reference.

With the development of vaccines based on the deletion of EHV4 gG and EHV1 gG genes, in addition to having the two gG's as capture antigens, it is necessary for either the individual filter paper for testing individual horse serurns or the 96-well or other formatted ELISAs to have a capture antigen to show that the horse has been immunized. Vaccines for the control of both EHV4 and EHV1 are combined vaccines i.e. they contain a mixture of both viruses, the antigen used can be either whole virus e.g. EHV4 or EHV1. The whole viruses are known to contain many cross reactive epitopes.

The invention also provides a basis for making recombinant DNA vaccines by inserting into the gG gene location genes encoding important antigens from other equine pathogens such as those from equine influenza virus, equine arteritis virus, equine rhinovirus and equine adenovirus among others. It is also claimed that the gG insertion site could be useful for the insertion of other protein genes to be delivered to horses such as those encoding adjuvants. The insertion of such other genes into the gG gene could follow deletion of part of the gG gene to make a gG negative mutant virus. It is evident particularly from the seemingly large amount of EHV4 gG secreted into the medium of infected cultures that the gG gene possesses a strong promoter which is favourable for high level expression of foreign genes.

Since modifications within the spirit and scope of the invention may be readily effected by persons skilled in the art, it is to be understood that the invention is not limited to the particular embodiment described, by way of exarnple, herein above.

TABLE 1

REACTIVITY OF INFECTED CELL CULTURE SUPERNATANTS IN ELISA

| | ELISA Titres | | | |
|---|---|---|---|---|
| Serum | EHV4/EHV1[a] | mock S/N[b] | EHV4 S/N | EHV1 S/N |
| SPF foal pre bleed (pool) | <1.5/<1.5 | <10 | <10 | <10 |
| SPF foal 1 (post E1) | 3.6/4.3 | <10 | 40 | 20 |
| SPF foal 2a (post E1) | 2.8/3.6 | <10 | 20 | <10 |
| SPF foal 2b (post E1 & E4) | 4.3/4.3 | <10 | 500 | 20 |
| SPF foal 3 (post E4) | 3.8/4.1 | <10 | 630 | 20 |
| post E4 serum No. 3 | 4.1/4.1 | <10 | 1000 | 40 |

[a]Purified EHV4 or EHV1 (10 $\mu$g/ml in coating buffer) was used to coat wells. Titres were determined from a titration curve and expressed as $\log_{10}$ of the reciprocal of the highest dilution of sera that gave an absorbance reading of at least twice the baseline reading.

[b]Either mock, EHV4 (E4) or EHV1 (E1) infected cell culture supernatant (S/N) was used to coat wells (diluted 1:5 in coating buffer). Titres are expressed as the reciprocal of the highest dilution of sera than gave an absorbance of at least twice the baseline reading.

TABLE 2

Reactivity of EHV4 gG and EHV1 gG GST-fusion proteins in ELISA

| | Immunising or infecting virus strain[a] | | ELISA titers[b] | | | | |
|---|---|---|---|---|---|---|---|
| | | | | | | GST-E4 gG | GST-E1 gG |
| Horse serum | EHV4 | EHV1 | EHV4[c] | EHV1 | GST only[d] | (aa287-374) | (aa288-350) |
| SPF foal pre (pool) | — | — | <30 | <30 | <10 | <10 | <10 |
| SPF foal 1 | — | 438/77 | 4,000 | 21,000 | 10 | 30 | 10,000 |
| SPF foal 2a | — | 438/77 | 630 | 4,000 | <10 | 15 | 1,000 |
| SPF foal 2b | 405/76 | 438/77 | 21,000 | 21,000 | <10 | 3,000 | 250 |
| SPF foal 3 | 405/76 | — | 6,300 | 13,000 | 50 | 1,500 | 150 |
| post-E4 No. 1 | 39/67 | — | 13,000 | 21,000 | 300 | 30,000 | 150 |
| post-E4 No. 2 | 39/67 | — | 6,300 | 6,300 | 300 | 30,000 | 300 |
| post-E4 No. 3 | 39/67 | — | 13,000 | 13,000 | 100 | 15,000 | 150 |
| abortion mare 1 | ? | 848/89 | 40,000 | 63,000 | 300 | 3,000 | 1,500 |
| abortion mare 2 | ? | 849/89 | ND[e] | ND | 50 | 10,000 | 3,000 |
| post EHV2 foal | — | — | ND | ND | 30 | 30 | 10 |

[a]SPF foals 1 and 3 were immunised with inactivated virus before challenge with the homologous live virus while all other horses received live virus via either experimental (SPF foal 2, post-E4 horses, post EHV2 foal) or natural infection (abortion mares). The immunisation and experimental infection protocols are described in references 23, 64 and the virus strains are described in references 56, 58.

[b]Titers were determined from a titration curve and expressed as the reciprocal of the highest dilution of serum that gave an absorbance reading of at least twice the baseline reading.

[c]Purified whole EHV4 or EHV1 (10 $\mu$g/ml) was used to coat wells.

[d]GST-fusion proteins prepared from *E. coli* transformed with parental pGEX (GST only), pEG4var (E4 gG aa287-374) and pEG1var (E1 gG aa288-350) were used to coat wells at 0.5 $\mu$g/ml.

[e]Not determined

We claim:

1. An isolated envelope glycoprotein G (gG) of equine herpesvirus (EHV) that elicits a type-specific response to equine herpesvirus 4 (EHV4), wherein said envelope glycoprotein G is EHV4 gG.

2. EHV4 gG according to claim 1, comprising 435 amino acid residues and having an unglycosylated Mr value of 48 kilodaltons.

3. EHV4 gG according to claim 2, consisting of the amino acid sequence of SEQ ID NO:2.

4. An isolated nucleotide sequence encoding EHV4 gG according to claim 3, consisting of the nucleotide sequence of SEQ ID NO: 1 or degeneracy equivalents of SEQ ID NO:1.

5. An EHV4 epitope that elicits a type-specific response to EHV4, comprising the amino acid sequence of SEQ ID NO:4 or a subsequence of SEO ID NO:4 that elicits a type-specific response to EHV4.

6. An EHV4 epitope according to claim 5, consisting of the amino acid sequence of SEQ ID NO:4.

7. An EHV4 epitope that elicits a type-specific response to EHV4, comprising the amino acid sequence of SEQ ID NO:5 or a subsequence of SEQ ID NO:5 that elicits a type-specific response to EHV4.

8. Plasmid vector pEG4, var.

9. An EHV1 epitope that elicits a type-specific response to EHV1, consisting of the amino acid sequence of SEQ ID NO:6, or a subsequence of SEQ ID NO:6 that elicits a type-specific response to EHV1.

10. An EHV1 epitope according to claim 9, consisting of the amino acid sequence of SEQ ID NO:6.

11. An EHV1 epitope that elicits a type-specific response to EHV1, consisting of the amino acid sequence of SEQ ID NO:7 or a subsequence of SEQ ID NO:7 that elicits a typespecific response to EHV1.

12. Plasmid vector pEG1var.

13. An immunogenic composition comprising an immunogenic amount of the EHV4 epitope according to any one of claims 5 to 7 in a physiologically acceptable vehicle.

14. An immunogenic composition comprising an immunogenic amount of the EHV1 epitope according to any one of claims 9 to 11 in a physiologically acceptable vehicle.

15. An immunological test kit for screening for EHV4 and EHV1 infection of a horse, comprising as capture antigens (1) an envelope glycoprotein comprising an EHV4 epitope that elicits a type-specific response to EHV4 and (2) an envelope glycoprotein comprising an EHV1 epitope that elicits a type-specific response to EHV1.

16. A hybridization nucleic acid probe specific for EHV1 gG gene selected from the group consisting of:

a probe consisting of the nucleotides encoding the amino acid sequence of SEQ ID NO:6 or a subsequence of SEQ ID NO:6 that elicits a type-specific response to EHV1, and a probe consisting of the nucleotides encoding the amino acid sequence of SEQ ID NO:7 or a subsequence of SEQ ID NO:7 that elicits a type-specific response to EHV1.

17. A hybridization nucleic acid probe specific for EHV4 gG gene selected from the group consisting of:

a probe encoding the amino acid sequence of SEQ ID NO:4 or a subsequence of SEQ ID NO:4 that elicits a type-specific response to EHV4, and a probe encoding the amino acid sequence of SEQ ID NO:5 or a subsequence of SEQ ID NO:5 that elicits a type-specific response to EHV4.

18. An isolated nucleotide sequence consisting of the nucleotides encoding the EHV4 gG according to claim 3.

19. An EHV4 epitope according to claim 7, consisting of the amino acid sequence of SEQ ID NO:5.

20. An EHV1 epitope according to claim 11, consisting of the amino acid sequence of SEQ ID NO:7.

21. The immunological test kit according to claim 15, wherein said EHV4 epitope is selected from the group consisting of:

an epitope comprising the amino acid sequence of SEQ ID NO:4 or a subsequence of SEQ ID NO:4 that elicits a type-specific response to EHV4, and an epitope comprising the amino acid sequence of SEQ ID NO:5 or a subsequence of SEQ ID NO:5 that elicits a type-specific response to EHV4.

22. The immunological test kit according to claim 15, wherein said EHV1 epitope is selected from the group consisting of:

an epitope comprising the amino acid sequence of SEQ ID NO:6 or a subsequence of SEQ ID NO:6 that elicits a type-specific response to EHV1, and an epitope comprising the amino acid sequence of SEQ ID NO:7 or a subsequence of SEQ ID NO:7 that elicits a type-specific response to EHV1.

23. An isolated envelope glycoprotein G (gG) of equine herpesvirus (EHV) that elicits a type-specific response to equine herpesvirus 4 (EHV4), wherein the envelope glycoprotein G is EHV4 gG encoded by the sequence of the exogenous DNA structural sequence of plasmid vector pEG4.1.

24. The EHV4 gG according to claim 23, produced by expressing the exogenous DNA structural sequence of plasmid vector pEG4.1 in a host.

25. The EHV4 gG according to claim 24, wherein the host is *E. coli.*

26. An EHV4 epitope that elicits a type-specific response to EHV4, wherein the epitope is encoded by the exogenous DNA structural sequence of plasmid vector pEG4.var.

27. The EHV4 epitope according to claim 26, produced by expressing the exogenous DNA structural sequence of plasmid vector pEG4.var in a host.

28. The EHV4 epitope according to claim 27, wherein the host is *E. coli.*

29. The immunological test kit according to claim 15, wherein the EHV4 epitope is encoded by the exogenous DNA structural sequence of plasmid vector pEG4.1.

30. The immunological test kit according to claim 15, wherein the EHV4 epitope is encoded by the exogenous DNA structural sequence of plasmid vector pEG4.var.

31. An EHV4 epitope that elicits a type-specific response to EHV4, comprising a subsequence of SEQ ID NO:2, wherein the subsequence elicits a type-specific response to EHV4, and wherein the epitope does not comprise full-length EHV4 gG.

32. An EHV4 epitope according to claim 31, consisting of a subsequence of SEQ ID NO:2, wherein the subsequence elicits a type-specific response to EHV4.

33. An isolated nucleotide sequence encoding the EHV4 epitope according to claim 31, wherein the nucleotide sequence does not encode full-length EHV4 gG.

34. An EHV1 epitope that elicits a type-specific response to EHV1, comprising the amino acid sequence of SEQ ID NO:6 or a subsequence of SEQ ID NO:6 that elicits a type-specific response to EHV1, wherein the EHV1 epitope is not the full-length EHV1 gG.

35. An EHV1 epitope that elicits a type-specific response to EHV1, comprising the amino acid sequence of SEQ ID NO:7 or a subsequence of SEQ ID NO:7 that elicits a type-specific response to EHV1, wherein the EHV1 epitope is not the full-length EHV1 gG.

36. An isolated nucleotide sequence encoding the EHV4 epitope according to claim 5, wherein the nucleotide sequence does not encode full-length EHV4 gG.

37. An isolated nucleotide sequence encoding the EHV4 epitope according to claim 7, wherein the nucleotide sequence does not encode full-length EHV4 gG.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
(A) LENGTH: 1507 base pairs
(B) TYPE: nucleic acid
(C) STRANDEDNESS: double
(D) TOPOLOGY: linear (ix) FEATURE:
(A) NAME/KEY: CDS
(B) LOCATION: 112..1416

(ix) FEATURE:
(A) NAME/KEY: mat_peptide
(B) LOCATION: 112..1416

(xi) SEQUENCE DESCRIPTION: SEQ ID NO:1:

```
ATTTGGGGTG GAGACGGCGT GGGCCGATAC TGTATAAAGT TGTACTACTT ACCAGCCCAG      60

TCAGTGTGCT GTAGTGCCAC CACCTGTAAA GCTGTGATAA GCTGCAGGCA T ATG TTG     117
                                                         Met Leu
                                                           1

GCT GTG GGA GCA ACT CTG TGT TTA CTG AGT TTC CTA ACT GGC GCT ACT      165
Ala Val Gly Ala Thr Leu Cys Leu Leu Ser Phe Leu Thr Gly Ala Thr
          5                  10                  15

GGA CGG CTA GCT CCT GAC GAC CTC TGC TAT GCA GAA CCC CGC AAA ACC      213
Gly Arg Leu Ala Pro Asp Asp Leu Cys Tyr Ala Glu Pro Arg Lys Thr
     20                  25                  30

GGT CCC ATG CCC CGC TCA AAA CCT AAA CAC CAA CCC CTA CTA TTT GAA      261
Gly Pro Met Pro Arg Ser Lys Pro Lys His Gln Pro Leu Leu Phe Glu
 35                  40                  45                  50

GCC CCA AAG GTT GCT CTT ACG GCA GAG TCA AAG GGT TGT CAA CTA ATA      309
Ala Pro Lys Val Ala Leu Thr Ala Glu Ser Lys Gly Cys Gln Leu Ile
                 55                  60                  65

TTG TTA GAC CCT CCA ATA GAC ATG GGC TAT CGC TTA GAG GAC AAG ATA      357
Leu Leu Asp Pro Pro Ile Asp Met Gly Tyr Arg Leu Glu Asp Lys Ile
             70                  75                  80

AAC GCT TCC ATT GCT TGG TTT TTT GAC TTT GGT AAT TGT CGA ATG CCC      405
Asn Ala Ser Ile Ala Trp Phe Phe Asp Phe Gly Asn Cys Arg Met Pro
         85                  90                  95

ATC GCA TAC AGA GAG TAC TAT GAT TGC GTT GGC AAC GCA ATC CCA TCT      453
Ile Ala Tyr Arg Glu Tyr Tyr Asp Cys Val Gly Asn Ala Ile Pro Ser
    100                 105                 110

CCA GAA ACA TGT GAT GGT TAC TCA TTT ACA CTT GTT AAA ACA GAG GGT      501
Pro Glu Thr Cys Asp Gly Tyr Ser Phe Thr Leu Val Lys Thr Glu Gly
115                 120                 125                 130

GTA GTT GAG TTT ACC ATC GTA AAC ATG AGC TTA CTG TTG CAG CCT GGA      549
Val Val Glu Phe Thr Ile Val Asn Met Ser Leu Leu Leu Gln Pro Gly
                135                 140                 145

ATA TAC GAC AGT GGA AGT TTT ATA TAC AGC GCC CTT CTA GAT ATG GAT      597
Ile Tyr Asp Ser Gly Ser Phe Ile Tyr Ser Ala Leu Leu Asp Met Asp
            150                 155                 160

GTA TTG ACT GGA CGC GTA ATT TTG AAC GTG GAG AAC GAC ACT AAC TAT      645
Val Leu Thr Gly Arg Val Ile Leu Asn Val Glu Asn Asp Thr Asn Tyr
        165                 170                 175

CCA TGC GGA ATG ACT CAC GGC CTC ACT GCG GAT GGC AAC ATC AAC GTA      693
Pro Cys Gly Met Thr His Gly Leu Thr Ala Asp Gly Asn Ile Asn Val
    180                 185                 190
```

-continued

```
GAT GAA ACC ACG CAC ACA ACC CCA CAT CCA CGT GCT GTC GGG TGT TTT      741
Asp Glu Thr Thr His Thr Thr Pro His Pro Arg Ala Val Gly Cys Phe
195                 200                 205                 210

CCA GAA CTC ATT AAC TTC GAT GCA TGG GAA AAC GTT ACA TTC GAA GAA      789
Pro Glu Leu Ile Asn Phe Asp Ala Trp Glu Asn Val Thr Phe Glu Glu
                215                 220                 225

ATG GGG ATA CCA GAC CCA AAC TCA TTT CTT GAT GAT GAG AGT GAT TAC      837
Met Gly Ile Pro Asp Pro Asn Ser Phe Leu Asp Asp Glu Ser Asp Tyr
            230                 235                 240

CCG AAT ACA ATG GAC TGT TAC TCG TGG GAT TTA TAC ACA TAT CCC AAA      885
Pro Asn Thr Met Asp Cys Tyr Ser Trp Asp Leu Tyr Thr Tyr Pro Lys
        245                 250                 255

AGC CTG AAG CAG GCA GAG GGG CCC CAA ACC TTG TTA ATA GGT GCA GTT      933
Ser Leu Lys Gln Ala Glu Gly Pro Gln Thr Leu Leu Ile Gly Ala Val
    260                 265                 270

GGA CTC AGA ATA CTC GCG CAA GCA TGG AAG TTT GTT GAA AAT GAA ACC      981
Gly Leu Arg Ile Leu Ala Gln Ala Trp Lys Phe Val Glu Asn Glu Thr
275                 280                 285                 290

TAC AGC AGC ATA CGC GCA GAT GCT AAG GAG TTG ATG TTA CAC AGC CAG     1029
Tyr Ser Ser Ile Arg Ala Asp Ala Lys Glu Leu Met Leu His Ser Gln
                295                 300                 305

TCC TGT ACA GCT GAT TCG TCG CAA GAA AGC ACA TCT ATG AAG AAT AAC     1077
Ser Cys Thr Ala Asp Ser Ser Gln Glu Ser Thr Ser Met Lys Asn Asn
            310                 315                 320

CCT ATT TAT TCA GAG GGG AGC CTC ATG CTA AAC GTT CAG CAC GAT GAC     1125
Pro Ile Tyr Ser Glu Gly Ser Leu Met Leu Asn Val Gln His Asp Asp
        325                 330                 335

AGC ATC CAC ACG GAA GGG ATG AAG AAT AAC CCT GTT TAT TCA GAG AGC     1173
Ser Ile His Thr Glu Gly Met Lys Asn Asn Pro Val Tyr Ser Glu Ser
    340                 345                 350

CTC ATG CTA AAC GTC CAG CAC GAT GAC AGC ATC CAC ACC GGG GGT GTG     1221
Leu Met Leu Asn Val Gln His Asp Asp Ser Ile His Thr Gly Gly Val
355                 360                 365                 370

TTG CAT GGC CTC CAA GAC TGC GAC AAC CAG CTC AAA ACT GTG TAT ATT     1269
Leu His Gly Leu Gln Asp Cys Asp Asn Gln Leu Lys Thr Val Tyr Ile
                375                 380                 385

TGC CTA GCT CTT ATT GGA CTC GGC ACA TGT GCC ATG ATA GGA CTA ATA     1317
Cys Leu Ala Leu Ile Gly Leu Gly Thr Cys Ala Met Ile Gly Leu Ile
            390                 395                 400

GTT TAC ATT TTT GTG CTA AGG TCA AAA ATA TCT TCC CAC AAT TTA TCG     1365
Val Tyr Ile Phe Val Leu Arg Ser Lys Ile Ser Ser His Asn Leu Ser
        405                 410                 415

CGC TCA CAA AAT GTA AAA CAT AGA AAC TAT CAT CGA CTT GAG TAC GTT     1413
Arg Ser Gln Asn Val Lys His Arg Asn Tyr His Arg Leu Glu Tyr Val
    420                 425                 430

GCA TAATACATGT CAAAATAAAA GTTAAAAATT AAACATTGTT GTCTGTAATA          1466
Ala
435

ACTGAGTGTG GTTTTAAAAA ATACTAAATC GCGGCAATGT T                       1507
```

(2) INFORMATION FOR SEQ ID NO:2:

(i) SEQUENCE CHARACTERISTICS:
(A) LENGTH: 435 amino acids
(B) TYPE: amino acid
(D) TOPOLOGY: linear (ii) MOLECULE TYPE: protein (xi) SEQUENCE DESCRIPTION: SEQ ID NO:2:

```
Met Leu Ala Val Gly Ala Thr Leu Cys Leu Leu Ser Phe Leu Thr Gly
  1               5                  10                  15
```

-continued

```
Ala Thr Gly Arg Leu Ala Pro Asp Asp Leu Cys Tyr Ala Glu Pro Arg
            20                  25                  30

Lys Thr Gly Pro Met Pro Arg Ser Lys Pro Lys His Gln Pro Leu Leu
        35                  40                  45

Phe Glu Ala Pro Lys Val Ala Leu Thr Ala Glu Ser Lys Gly Cys Gln
    50                  55                  60

Leu Ile Leu Leu Asp Pro Pro Ile Asp Met Gly Tyr Arg Leu Glu Asp
65                  70                  75                  80

Lys Ile Asn Ala Ser Ile Ala Trp Phe Phe Asp Phe Gly Asn Cys Arg
                85                  90                  95

Met Pro Ile Ala Tyr Arg Glu Tyr Tyr Asp Cys Val Gly Asn Ala Ile
            100                 105                 110

Pro Ser Pro Glu Thr Cys Asp Gly Tyr Ser Phe Thr Leu Val Lys Thr
        115                 120                 125

Glu Gly Val Val Glu Phe Thr Ile Val Asn Met Ser Leu Leu Leu Gln
    130                 135                 140

Pro Gly Ile Tyr Asp Ser Gly Ser Phe Ile Tyr Ser Ala Leu Leu Asp
145                 150                 155                 160

Met Asp Val Leu Thr Gly Arg Val Ile Leu Asn Val Glu Asn Asp Thr
                165                 170                 175

Asn Tyr Pro Cys Gly Met Thr His Gly Leu Thr Ala Asp Gly Asn Ile
            180                 185                 190

Asn Val Asp Glu Thr Thr His Thr Thr Pro His Pro Arg Ala Val Gly
        195                 200                 205

Cys Phe Pro Glu Leu Ile Asn Phe Asp Ala Trp Glu Asn Val Thr Phe
    210                 215                 220

Glu Glu Met Gly Ile Pro Asp Pro Asn Ser Phe Leu Asp Asp Glu Ser
225                 230                 235                 240

Asp Tyr Pro Asn Thr Met Asp Cys Tyr Ser Trp Asp Leu Tyr Thr Tyr
                245                 250                 255

Pro Lys Ser Leu Lys Gln Ala Glu Gly Pro Gln Thr Leu Leu Ile Gly
            260                 265                 270

Ala Val Gly Leu Arg Ile Leu Ala Gln Ala Trp Lys Phe Val Glu Asn
        275                 280                 285

Glu Thr Tyr Ser Ser Ile Arg Ala Asp Ala Lys Glu Leu Met Leu His
    290                 295                 300

Ser Gln Ser Cys Thr Ala Asp Ser Ser Gln Glu Ser Thr Ser Met Lys
305                 310                 315                 320

Asn Asn Pro Ile Tyr Ser Glu Gly Ser Leu Met Leu Asn Val Gln His
                325                 330                 335

Asp Asp Ser Ile His Thr Glu Gly Met Lys Asn Asn Pro Val Tyr Ser
            340                 345                 350

Glu Ser Leu Met Leu Asn Val Gln His Asp Asp Ser Ile His Thr Gly
        355                 360                 365

Gly Val Leu His Gly Leu Gln Asp Cys Asp Asn Gln Leu Lys Thr Val
    370                 375                 380

Tyr Ile Cys Leu Ala Leu Ile Gly Leu Gly Thr Cys Ala Met Ile Gly
385                 390                 395                 400

Leu Ile Val Tyr Ile Phe Val Leu Arg Ser Lys Ile Ser Ser His Asn
                405                 410                 415

Leu Ser Arg Ser Gln Asn Val Lys His Arg Asn Tyr His Arg Leu Glu
            420                 425                 430

Tyr Val Ala
```

435

(2) INFORMATION FOR SEQ ID NO:3:

(i) SEQUENCE CHARACTERISTICS:
(A) LENGTH: 411 amino acids
(B) TYPE: amino acid
(C) STRANDEDNESS: single
(D) TOPOLOGY: linear (xi) SEQUENCE DESCRIPTION: SEQ ID NO:3:

```
Met Leu Thr Val Leu Ala Ala Leu Ser Leu Leu Ser Leu Leu Thr Ser
1               5                   10                  15

Ala Thr Gly Arg Leu Ala Pro Asp Glu Leu Cys Tyr Ala Glu Pro Arg
            20                  25                  30

Arg Thr Gly Ser Pro Pro Asn Thr Gln Pro Glu Arg Pro Pro Val Ile
        35                  40                  45

Phe Glu Pro Pro Thr Ile Ala Ile Lys Ala Glu Ser Lys Gly Cys Glu
    50                  55                  60

Leu Ile Leu Leu Asp Pro Pro Ile Asp Val Ser Tyr Arg Arg Glu Asp
65                  70                  75                  80

Lys Val Asn Ala Ser Ile Ala Trp Phe Phe Asp Phe Gly Ala Cys Arg
                85                  90                  95

Met Pro Ile Ala Tyr Arg Glu Tyr Tyr Gly Cys Ile Gly Asn Ala Val
            100                 105                 110

Pro Ser Pro Glu Thr Cys Asp Ala Tyr Ser Phe Thr Leu Ile Arg Thr
        115                 120                 125

Glu Gly Ile Val Glu Phe Thr Ile Val Asn Met Ser Leu Leu Phe Gln
    130                 135                 140

Pro Gly Ile Tyr Asp Ser Gly Asn Phe Ile Tyr Ser Val Leu Leu Asp
145                 150                 155                 160

Tyr His Ile Phe Thr Gly Arg Val Thr Leu Glu Val Glu Lys Asp Thr
                165                 170                 175

Asn Tyr Pro Cys Gly Met Ile His Gly Leu Thr Ala Tyr Gly Asn Ile
            180                 185                 190

Asn Val Asp Glu Thr Met Asp Asn Ala Ser Pro His Pro Arg Ala Val
        195                 200                 205

Gly Cys Phe Pro Glu Pro Ile Asp Asn Glu Ala Trp Ala Asn Val Thr
    210                 215                 220

Phe Thr Glu Leu Gly Ile Pro Asp Pro Asn Ser Phe Leu Asp Asp Glu
225                 230                 235                 240

Gly Asp Tyr Pro Asn Ile Ser Asp Cys His Ser Trp Glu Ser Tyr Thr
                245                 250                 255

Tyr Pro Asn Thr Leu Arg Gln Ala Thr Gly Pro Gln Thr Leu Leu Val
            260                 265                 270

Gly Ala Val Gly Leu Arg Ile Leu Ala Gln Ala Trp Lys Phe Val Gly
        275                 280                 285

Asp Glu Thr Tyr Asp Thr Ile Arg Ala Glu Ala Lys Asn Leu Glu Thr
    290                 295                 300

His Val Pro Ser Ser Ala Ala Glu Ser Ser Leu Glu Asn Gln Ser Thr
305                 310                 315                 320

Gln Glu Glu Ser Asn Ser Pro Glu Val Ala His Leu Arg Ser Val Asn
                325                 330                 335

Ser Asp Asp Ser Thr His Thr Gly Gly Ala Ser Asn Gly Ile Gln Asp
            340                 345                 350

Cys Asp Ser Gln Leu Lys Thr Val Tyr Ala Cys Leu Ala Leu Ile Gly
```

-continued

```
        355                 360                 365

Leu Gly Thr Cys Ala Met Ile Gly Leu Ile Val Tyr Ile Cys Val Leu
    370                 375                 380

Arg Ser Lys Leu Ser Ser Arg Asn Phe Ser Arg Ala Gln Asn Val Lys
385                 390                 395                 400

His Arg Asn Tyr Gln Arg Leu Glu Tyr Val Ala
                405                 410
```

(2) INFORMATION FOR SEQ ID NO:4:

(i) SEQUENCE CHARACTERISTICS:
(A) LENGTH: 88 amino acids
(B) TYPE: amino acid
(C) STRANDEDNESS: single
(D) TOPOLOGY: linear (xi) SEQUENCE DESCRIPTION: SEQ ID NO:4:

```
Glu Asn Glu Thr Tyr Ser Ser Ile Arg Ala Asp Ala Lys Glu Leu Met
1               5                   10                  15

Leu His Ser Gln Ser Cys Thr Ala Asp Ser Ser Gln Glu Ser Thr Ser
            20                  25                  30

Met Lys Asn Asn Pro Ile Tyr Ser Glu Gly Ser Leu Met Leu Asn Val
        35                  40                  45

Gln His Asp Asp Ser Ile His Thr Glu Gly Met Lys Asn Asn Pro Val
    50                  55                  60

Tyr Ser Glu Ser Leu Met Leu Asn Val Gln His Asp Asp Ser Ile His
65                  70                  75                  80

Thr Gly Gly Val Leu His Gly Leu
                85
```

(2) INFORMATION FOR SEQ ID NO:5:

(i) SEQUENCE CHARACTERISTICS:
(A) LENGTH: 25 amino acids
(B) TYPE: amino acid
(C) STRANDEDNESS: single
(D) TOPOLOGY: linear (xi) SEQUENCE DESCRIPTION: SEQ ID NO:5:

```
Lys Thr Gly Pro Met Pro Arg Ser Lys Pro Lys His Gln Pro Leu Leu
1               5                   10                  15

Phe Glu Ala Pro Lys Val Ala Leu Thr
            20                  25
```

(2) INFORMATION FOR SEQ ID NO:6:

(i) SEQUENCE CHARACTERISTICS:
(A) LENGTH: 63 amino acids
(B) TYPE: amino acid
(C) STRANDEDNESS: single
(D) TOPOLOGY: linear (xi) SEQUENCE DESCRIPTION: SEQ ID NO:6:

```
Gly Asp Glu Thr Tyr Asp Thr Ile Arg Ala Glu Ala Lys Asn Leu Glu
1               5                   10                  15

Thr His Val Pro Ser Ser Ala Ala Glu Ser Ser Leu Glu Asn Gln Ser
            20                  25                  30

Thr Gln Glu Glu Ser Asn Ser Pro Glu Val Ala His Leu Arg Ser Val
        35                  40                  45

Asn Ser Asp Asp Ser Thr His Thr Gly Gly Ala Ser Asn Gly Ile
    50                  55                  60
```

-continued (2) INFORMATION FOR SEQ ID NO:7:

(i) SEQUENCE CHARACTERISTICS:
(A) LENGTH: 25 amino acids
(B) TYPE: amino acid
(C) STRANDEDNESS: single
(D) TOPOLOGY: linear (xi) SEQUENCE DESCRIPTION: SEQ ID NO:7:

```
Arg Thr Gly Ser Pro Pro Asn Thr Gln Pro Glu Arg Pro Pro Val Ile
1               5                   10                  15

Phe Glu Pro Pro Thr Ile Ala Ile Lys
            20                  25
```

(2) INFORMATION FOR SEQ ID NO:8:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:8:

CGGGATCCAT GTTGACTGTC TTAGC 25

(2) INFORMATION FOR SEQ ID NO:9:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:9:

CGGGATCCTA AGCAACGTAC TCAAG 25

(2) INFORMATION FOR SEQ ID NO:10:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:10:

GAAAATGAAA CCTACAG 17

(2) INFORMATION FOR SEQ ID NO:11:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:11:

TGGAGGCCAT GCAACAC 17

(2) INFORMATION FOR SEQ ID NO:12:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:12:

-continued

```
GGTGACGAAA CATACGA                                                    17


(2) INFORMATION FOR SEQ ID NO:13:

     (i) SEQUENCE CHARACTERISTICS:
          (A) LENGTH: 17 base pairs
          (B) TYPE: nucleic acid
          (C) STRANDEDNESS: single
          (D) TOPOLOGY: linear

    (xi) SEQUENCE DESCRIPTION: SEQ ID NO:13:

TGGATGCCGT TCGACGC                                                    17
```